(12) United States Patent
Kojima et al.

(10) Patent No.: US 7,329,844 B2
(45) Date of Patent: Feb. 12, 2008

(54) PRISMATIC CERAMIC HEATER FOR HEATING GAS SENSOR ELEMENT, PRISMATIC GAS SENSOR ELEMENT IN MULTILAYERED STRUCTURE INCLUDING THE PRISMATIC CERAMIC HEATER, AND METHOD FOR MANUFACTURING THE PRISMATIC CERAMIC HEATER AND PRISMATIC GAS SENSOR ELEMENT

(75) Inventors: Takao Kojima, Aichi (JP); Keisuke Makino, Aichi (JP); Shinya Awano, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 939 days.

(21) Appl. No.: 10/374,056

(22) Filed: Feb. 27, 2003

(65) Prior Publication Data

US 2003/0159928 A1    Aug. 28, 2003

(30) Foreign Application Priority Data

Feb. 28, 2002  (JP) ............................. 2002-054554

(51) Int. Cl.
*H05B 3/44* (2006.01)
(52) U.S. Cl. ..................................................... 219/544
(58) Field of Classification Search ................ 219/544, 219/543, 538, 542; 204/410, 424, 426; 205/789
See application file for complete search history.

(56) References Cited

U.S. PATENT DOCUMENTS

| | | | |
|---|---|---|---|
| 4,824,549 A * | 4/1989 | Hamada et al. | ............. 204/410 |
| 5,419,828 A | 5/1995 | Nakano et al. | |
| 5,507,937 A * | 4/1996 | Renz et al. | .................. 204/426 |
| 5,820,745 A * | 10/1998 | Van Geloven | .............. 205/789 |
| 6,136,170 A * | 10/2000 | Inoue et al. | ................. 204/424 |
| 6,210,552 B1 | 4/2001 | Mizutani et al. | |

FOREIGN PATENT DOCUMENTS

| | | |
|---|---|---|
| CN | 1329247 A | 1/2002 |
| JP | 4-13961 | 1/1992 |
| JP | 5-43495 | 6/1993 |
| JP | 7-120429 | 5/1995 |
| JP | 8-201337 | 8/1996 |
| JP | 9-264871 | 10/1997 |
| JP | 11-160273 | 6/1999 |
| JP | 2000-180397 | 6/2000 |
| JP | 2001-281210 | 10/2001 |

* cited by examiner

*Primary Examiner*—Daniel Robinson
(74) *Attorney, Agent, or Firm*—Sughrue Mion, PLLC

(57) ABSTRACT

A prismatic ceramic heater for heating a gas sensor element includes a heating resistor embedded in ceramic, and has a substantially rectangular cross section. At least part of a longitudinally extending edge portion of the prismatic ceramic heater is located in the vicinity of the heating resistor. This part of the longitudinally extending edge portion is coated with a porous protective layer. The protective layer has a thickness not less than 20 μm and a curved surface of a curvature radius not less than 10 μm. The protective layer prevents cracking induced by contact with water.

14 Claims, 10 Drawing Sheets

PRISMATIC CERAMIC HEATER FOR HEATING GAS SENSOR ELEMENT, PRISMATIC GAS SENSOR ELEMENT IN MULTILAYERED STRUCTURE INCLUDING THE PRISMATIC CERAMIC HEATER, AND METHOD FOR MANUFACTURING THE PRISMATIC CERAMIC HEATER AND PRISMATIC GAS SENSOR ELEMENT

BACKGROUND OF THE INVENTION

1. Field of the Invention

The present invention relates to a gas sensor, such as an oxygen sensor, an A/F sensor, an $NO_x$ sensor, or an HC sensor, for use in, for example, controlling exhaust gas from an internal combustion engine of an automobile. More particularly, the invention relates to a prismatic multilayered gas sensor element; a prismatic ceramic heater of a substantially rectangular cross section for heating the prismatic multilayered gas sensor element; a prismatic multilayered gas sensor element to be arranged integrally with the prismatic ceramic heater; a method for manufacturing the prismatic ceramic heater and the prismatic multilayered gas sensor element; and a gas sensor including the prismatic ceramic heater and/or the prismatic multilayered gas sensor element. The invention further relates to a method for manufacturing a prismatic ceramic heater of a substantially rectangular cross section for heating a gas sensor and a prismatic gas sensor element including the prismatic ceramic heater. Specifically, the invention is applied to a prismatic ceramic heater of a substantially rectangular cross section configured such that a heating resistor is embedded in a ceramic laminate, or to a prismatic gas sensor element configured such that a prismatic ceramic heater including an embedded heating resistor and an oxygen-ion-conductive solid electrolyte layer are arranged in layers. More particularly, the invention relates to a prismatic ceramic heater and a prismatic multilayered gas sensor element, each of which has a substantially rectangular cross section and includes a protective layer for preventing cracking which could otherwise result from contact with a water droplet; a method for manufacturing the prismatic ceramic heater and the prismatic multilayered gas sensor element; and a gas sensor including the ceramic heater and/or the multilayered gas sensor element.

2. Description of the Related Art

Various sensors (hereinafter may be referred to as "gas sensor elements"), such as oxygen sensors, HC sensors, and $NO_x$ sensors, have been used to measure the concentration of a certain gas, such as an oxygen, a hydrocarbon (HC) or nitrogen oxides ($NO_x$), contained in high-temperature exhaust gas emitted from an internal combustion engine of an automobile. Generally, such sensors use zirconia ceramic, which is an oxygen-ion-conductive solid electrolyte, to form an oxygen sensor cell for detecting the partial pressure of oxygen contained in exhaust gas. However, zirconia generally becomes oxygen-ion conductive only at 300° C. or higher. Therefore, in order to quickly activate an oxygen sensor cell and/or an oxygen-pumping cell of a gas sensor element, there has been proposed a prismatic multilayered sensor element including a ceramic heater having an embedded heating resistor. The multilayered gas sensor element assumes a prismatic shape for enabling mass production. Specifically, prismatic elements can be mass-produced by the steps of joining a ceramic-heater-forming green sheet and a sensor-cell-forming zirconia green sheet into a multilayered green sheet, and forming a number of prismatic elements from the multilayered green sheet through cutting or blanking.

Exhaust gas passing through an exhaust pipe of an internal combustion engine contains substances other than gas, such as water droplets and oil droplets. Upon contact with such a substance, particularly with a water droplet, a sensor element may crack or break. Since the sensor element or a ceramic heater is exposed to heat of an engine, contact with a water droplet or the like raises a great temperature difference between a portion in contact with the water droplet and its adjacent portion, thereby inducing thermal shock. Such thermal shock may cause a breakage of the sensor element or the ceramic heater. Conventionally, two methods for solving this problem have been employed. In one of these methods, a protector having a number of fine ventilation holes formed therein is deployed around the sensor element or the ceramic heater in such a manner as not to hinder the response of the sensor element. However, the protector fails to provide protection against a liquid substance that readily passes through the ventilation holes. In the other method, the surface of a sensor element is coated with a porous protective layer as disclosed in Japanese Patent Application Laid-Open (kokai) Nos. H04-13961, H07-120429, and 2001-281210.

However, various environmental tests which the present inventors have conducted for feasibility study have revealed the following: even when the surface of a prismatic sensor element is coated with a porous protective layer by a method disclosed or suggested in the above-mentioned publications, contact of a liquid substance, such as a water droplet or oil, with a longitudinally extending edge portion defined by the upper or lower surface and a side surface of the prismatic sensor element, particularly with part of the edge portion located in the vicinity of a heating resistor, induces cracking at the edge portion, and the crack develops to break the prismatic sensor element. This cracking problem arises because the conventional methods do not pay attention to water-induced-shock resistance of such an edge portion. The findings from the tests indicate that, in order to completely prevent cracking or breakage of a prismatic ceramic heater or multilayered sensor element (particularly, a prismatic multilayered sensor element configured such that a ceramic heater and a sensor cell are integrally formed through simultaneous firing), water-induced-shock resistance of a porous protective layer itself must be improved; and the porous protective layer formed on the edge portion is apt to detach or exfoliate upon occurrence of an abrupt thermal change induced by contact with a water droplet or the like.

SUMMARY OF THE INVENTION

The present invention has been achieved to solve the above-mentioned problems.

A primary object of the present invention is to improve water-induced-shock resistance of an edge portion of a prismatic ceramic heater for heating a gas sensor, and/or that of a prismatic multilayered ceramic sensor using the prismatic ceramic heater.

A second object of the present invention is to provide a prismatic ceramic heater for heating a gas sensor which is free from cracking or breakage of an edge portion even upon contact with a liquid substance such as a water droplet, as well as to provide a prismatic ceramic sensor using the prismatic ceramic heater and being free from such cracking or breakage.

A third object of the present invention is to provide a prismatic ceramic heater for heating a gas sensor in which a porous protective layer resistant to exfoliation; i.e., a porous protective layer having enhanced exfoliation resistance is formed on a longitudinally extending edge portion of the ceramic heater, as well as to provide a prismatic multilayered ceramic sensor including a prismatic ceramic heater in which a porous protective layer having enhanced exfoliation resistance is formed on a longitudinally extending edge portion of the ceramic sensor.

A fourth object of the present invention is to provide a method for manufacturing a prismatic ceramic heater for heating a gas sensor, and/or a prismatic multilayered ceramic sensor, the prismatic ceramic heater and the prismatic multilayered ceramic sensor being configured such that, even upon contact with a liquid substance such as a water droplet, cracking does not occur, and a porous protective layer does not exfoliate.

In the present invention, the expression "prismatic laminate" refers to a prismatic ceramic heater configured such that a heating resistor is embedded in an alumina laminate, or a prismatic multilayered ceramic sensor element configured such that a ceramic heater including an embedded heating resistor, and an oxygen-ion-conductive solid electrolyte layer of zirconia are arranged in layers.

(A): A prismatic ceramic heater for heating a gas sensor element according to the present invention has at least one of features (A1) to (A5) described below. The respective features provide different advantages.

(A1): The prismatic ceramic heater is configured such that a heating resistor and its leads are embedded in a prismatic ceramic substrate of a substantially rectangular cross section. At least part of a longitudinally extending edge portion of the ceramic substrate, the part being located in the vicinity of the heating resistor, is coated with a porous protective layer of ceramic having a thickness of 20-500 µm and adapted to prevent cracking of the edge portion which could otherwise result from contact with water.

The porosity of the porous protective layer of ceramic is preferably 15%-65%, more preferably 30%-60%. The thickness of the porous protective layer of ceramic is preferably 50-300 µm. The ceramic heater substrate may be an alumina ceramic laminate configured such that a heating resistor formed predominantly from a noble metal and/or an ion-migration-preventing electrode (hereinafter may be referred to as an "a conductor for retaining ionized elements") for preventing a deterioration of the heating resistor are embedded therein. The porous protective layer may cover the entire surface of the ceramic substrate instead of covering only an edge portion.

Feature (A1) provides the following advantage. Through forming a porous ceramic having a porosity of 15%-65% and a thickness not less than 20 µm on a longitudinally extending edge portion, which is apt to suffer cracking as a result of contact with a water droplet, particularly on part of the edge portion located in the vicinity of the heating resistor provided for activating the sensor, the prismatic ceramic heater is protected from cracking which could otherwise result from contact with water; i.e., water-induced-shock resistance of the prismatic ceramic heater can be enhanced. When the porosity or thickness falls below the lower-limit, the porous protective layer fails to absorb stress induced by thermal shock which, in turn, is induced by contact with water, thereby failing to prevent cracking in an edge portion of the ceramic heater. When the porosity or thickness is in excess of the upper limit, the intergranular bonding strength of the porous ceramic drops considerably, and/or the porous ceramic is apt to exfoliate from an edge portion (A2): The porous protective layer of ceramic is formed on the surface of an edge portion in such a manner as to assume a roundly curved surface of a curvature radius not less than 10 µm, preferably not less than 50 µm. As viewed on a cross section of an edge portion of the ceramic heater, the surface of the porous protective layer that covers the edge portion having an angle of about 90 degrees forms an arcuate curve having a curvature radius of at least 10 µm.

Feature (A2) provides the following advantage. Impartment of the roundly curved surface to the porous protective layer not only prevents chipping of the porous protective layer or dropping-off of ceramic particles of the porous protective layer which could otherwise result from subjection to a mechanical, external force, but also uniformly distributes over the entire curved surface the force of resistance to thermal shock induced by contact with water, whereby the porous protective layer provides enhanced water-induced-shock resistance for the edge portion.

(A3): Preferably, the porous protective layer assumes a multilayered structure including at least a joining layer and a surface layer.

Feature (A3) provides the following advantage. A function of enhancing a joining force exerted mainly between the porous protective layer and an edge portion is imparted to the bottom joining layer to be firmly fixed to the edge portion, whereas a function of enhancing absorption of water-induced thermal shock (water-induced-shock resistance) is imparted to the surface layer, thereby enhancing exfoliation resistance and water-induced-shock resistance of the porous protective layer as a whole.

The point is that an average pore diameter of the joining layer (i.e., the bottom layer to be firmly fixed to an edge portion) is greater than, preferably at least two times, that of the other portion of the porous protective layer. The thus-configured joining layer stably maintains the role of anchoring (firmly fixing) the protective layer to an edge portion in the process of manufacture and in subsequent employment in an actual heat-cycling environment.

(A4): Preferably, a lower-layer portion of the porous protective layer is formed from ceramic particles which are firmly fixed to an edge portion of a ceramic heater substrate by means of being fired simultaneously with the ceramic heater substrate, whereas an upper-layer portion of the porous protective layer is formed from ceramic particles which are firmly fixed to the lower-layer portion through firing subsequent to the simultaneous firing. In this case, the upper-layer portion is fired at a temperature lower than that for firing the lower-layer portion.

Feature (A4) provides the following advantage. The bottom layer of the porous protective layer and the ceramic heater are simultaneously fired to thereby strengthen anchorage of the porous protective layer to the ceramic heater, thereby enhancing the advantage provided by feature (A3) described above.

(A5): The porous protective layer comprises a plurality of porous layers which differ in water-induced-shock resistance. Specifically, a plurality of porous ceramic layers of different pore diameters, and of different porosities and/or particle diameters are formed on at least an edge portion.

Feature (A5) provides the following advantage. Feature (A5) enables effective adjustment of enhancement in absorption or alleviation of thermal shock whose intensity depends on the size of a water droplet coming into contact with the ceramic heater; i.e., effective adjustment in a mechanism to absorb thermal shock which is induced by contact with a water droplet and potentially induces cracking.

(B): A prismatic gas sensor element of the present invention has at least one of features (B1) to (B5) described below. The respective features provide different advantages.

(B1): The prismatic gas sensor element assumes a multilayered structure including a ceramic heater, a solid electrolyte ceramic layer, and an electrode-protecting layer. The ceramic heater is configured such that a heating resistor and its leads are embedded in a ceramic substrate; the solid electrolyte ceramic layer partially constitutes a sensor cell; and the electrode-protecting layer covers a sensor cell electrode. In an edge portion of the prismatic gas sensor element having an angle of about 90 degrees and extending in the longitudinal direction of the element, at least part of the edge portion located in the vicinity of the heating resistor is coated with a porous protective layer of ceramic having a porosity of 15%-65% and a thickness of 20-500 μm and adapted to prevent cracking of the edge portion which could otherwise result from contact with water.

Preferably, the porous protective layer of ceramic has a porosity of 30%-60% and a thickness of 50-300 μm. The porous protective layer may cover the entire surface of the ceramic substrate instead of covering only an edge portion. The solid electrolyte ceramic layer may be in a multilayered structure including an oxygen-ion-conductive zirconia ceramic layer and a plurality of insulating layers. The substrate of the ceramic heater to be overlaid on the solid electrolyte ceramic layer is an alumina ceramic laminate configured such that a heating resistor formed predominantly from a noble metal, and/or an ion-migration-preventing electrode for preventing a deterioration of the heating resistor are embedded therein.

Feature (B1) provides the same advantage as feature (A1).

(B2): The porous protective layer is formed on the surface of an edge portion in such a manner as to assume a roundly curved surface of a curvature radius not less than 10 μm, preferably not less than 50 μm. As viewed on a cross section of an edge portion of the prismatic gas sensor element, the surface of the porous protective layer that covers the edge portion having an angle of about 90 degrees forms an arcuate curve having a curvature radius of at least 10 μm.

Feature (B2) provides the same advantage as feature (A2).

(B3): Preferably, the porous protective layer assumes a multilayered structure including at least a joining layer and a surface layer. An average pore diameter of the joining layer (i.e., the bottom layer to be firmly fixed to an edge portion) is greater than, preferably at least two times, that of the other portion of the porous protective layer.

Feature (B3) provides the same advantage as feature (A3).

(B4): Preferably, a lower-layer portion of the porous protective layer is formed from ceramic particles which are firmly fixed to an edge portion of the prismatic gas sensor element by means of being fired simultaneously with the gas sensor element, whereas an upper-layer portion of the porous protective layer is formed from ceramic particles which are firmly fixed to the lower-layer portion through firing subsequent to the simultaneous firing. In this case, the upper-layer portion is fired at a temperature lower than that for firing the lower-layer portion.

Feature (B4) provides the same advantage as feature (A4).

(B5): The porous protective layer comprises a plurality of porous layers which differ in water-induced-shock resistance. Specifically, a plurality of porous ceramic layers of different pore diameters, and of different porosities and/or particle diameters are formed on at least an edge portion.

Feature (B5) provides the same advantage as feature (A5).

Preferably, in order to prevent a deterioration or breakage of a heating portion of the heating resistor embedded in the ceramic of the ceramic heater which could otherwise result from migration of divalent and trivalent metal ions (e.g., $Mg^{2+}$ and $Ca^{2+}$ from oxides such as MgO and CaO) present in the ceramic, an ion-migration-preventing electrode (a conductor for retaining ionized elements)—to which an electric potential equal to or lower than that applied to the heating resistor is applied—is embedded in the ceramic in the vicinity of the heating resistor. In the prismatic ceramic heater and the prismatic gas sensor element of the present invention, the ion-migration-preventing electrode is disposed between the heating resistor and the porous protective layer, for providing a preventive effect as described below. Since metal ions are also present in the porous protective layer, migrating metal ions may recombine with oxygen to thereby form a weak glass phase (glass). Even when the glass phase cracks as a result of contact between water and the ceramic heater, the cracking position is not located between the heating resistor and a solid electrolyte layer used to form the sensor cell.

(C): The present invention provides a method for manufacturing a prismatic ceramic heater for heating a gas sensor element, or a prismatic gas sensor element, the ceramic heater and the gas sensor element including a porous protective layer for preventing cracking in an edge portion, which could otherwise result from contact with water. The method includes at least the following steps (C1) to (C5):

(C1): a step for arranging at least a first ceramic green sheet and a second ceramic green sheet in layers in order to form a layered sheet;

(C2): a step for forming a green prismatic laminate having a longitudinally extending edge portion from said layered sheet;

(C3): a step for firing said green prismatic laminate to obtain a prismatic laminate;

(C4): a step for preparing a ceramic material powder and applying said ceramic material powder to a longitudinally extending edge portion of said prismatic laminate such that at least part of said longitudinally extending edge portion to be exposed to a gas to be measured is coated with a porous protective layer having a porosity of 15%-65% and a thickness of 20-500 μm; and (C5): a step for firmly fixing said applied ceramic powder to said edge portion through firing.

The manufacturing method (C) provides the following advantage. The water-induced-shock resistant porous protective layer is firmly formed on an edge portion of the prismatic laminate used to form the prismatic ceramic sensor or the prismatic gas sensor element, in a consistent manner; i.e., with good reproducibility.

In the step (C4) of the manufacturing method (C), by means of using a mixture of a ceramic powder and a porosity-enhancing agent as the green ceramic material powder, the porous protective layer formed through firing can assume a porosity or an average pore diameter falling within a targeted range, in a uniform, consistent manner. This advantage is enhanced by using as a porosity-enhancing agent a carbon powder or organic material powder which has uniform particle size and burns out when heated.

The steps of the manufacturing method (C) may be performed in sequence (P1) or (P2) represented below by use of arrows:

sequence (P1): (C1)→(C2)→(C4)→(C3)→(C5); and
sequence (P2): (C1)→(C2)→(C3)→(C4)→(C5).

The feature of the sequence (P1) resides in simultaneously firing (or rather to firing) the green prismatic laminate and the green ceramic powder applied to the laminate. The sequence (P1) provides an advantage in that the porous protective layer is firmly fixed to an edge portion through firing. However, the sequence (P1) involves the following disadvantage: since firing conditions must be strictly controlled in consideration of difference in firing contraction coefficient between the laminate and the material powder, a limit may be imposed on the thickness of the green ceramic powder layer to be formed in step (C4); therefore, a required thickness may fail to be imparted to the green ceramic powder layer.

The feature of the sequence (P2) resides in forming the porous protective layer through firing on an edge portion of the prismatic laminate which has been fired beforehand. Therefore, in contrast to the case of sequence (P1), there is no need to consider a limit imposed on the thickness of the green ceramic powder layer, which is to become the porous protective layer. However, the sequence (P2) involves the following disadvantage: the intergranular bonding strength of the porous protective layer may be weakened, or the anchoring strength of the porous protective layer may be weakened in relation to fixation to the prismatic laminate.

Preferably, the steps of the manufacturing method (C) are performed in the following sequence (P3):

sequence (P3): (C1)→(C2)→(C4)→(C3)→(C4)→(C5).

The sequence (P3) has the following feature: the green laminate and the green ceramic material layer are fired simultaneously so as to form a portion of the porous protective layer as viewed in the thickness direction of the porous protective layer, and subsequently the green ceramic powder is applied and fired at a temperature lower than the temperature employed in simultaneous firing so as to form the remaining portion of the porous protective layer. The simultaneous firing temperature is about 1,350°C. to 1,600° C., preferably 1,450° C. to 1,550° C.

The sequence (P3) provides the following advantage. Since a lower-layer portion (at least a bottom joining layer) of the porous protective layer and the prismatic laminate are formed through simultaneous firing, the lower-layer portion of the porous protective layer is very firmly fixed to an edge portion of the prismatic laminate. Also, an upper-layer portion (at least a surface layer) of the porous protective layer is firmly fixed through firing to the lower-layer portion of the porous protective layer. As a result, the porous protective layer of a predetermined thickness having excellent water-induced-shock resistance and exfoliation resistance is readily obtained.

Preferably, in the above-described sequences (P1) and (P3), step (C4) is performed before step (C2). Specifically, a slit used to form part of an edge portion is formed in the layered sheet of the first and second green ceramic sheets. The slit is filled with a ceramic material powder, followed by cutting along the center of the slit. As a result, a green prismatic laminate is formed such that its edge portions are covered with the ceramic material powder. This sequence is suited for mass production.

In the above-described sequences (P1) to (P3), a porosity-enhancing agent (preferably assuming the form of powder), such as carbon, sawdust, and wax, which burns out at the time of firing and forms pores, is mixed in an amount of 30%-70% by volume with the ceramic material powder (alumina powder or spinel powder). By use of such a porosity-enhancing agent, the porous protective layer of ceramic having a porosity of 15%-65% and a thickness of 20-500 μm as required in the present invention and having excellent water-induced-shock resistance, joining property, and strength is consistently formed on an edge portion.

Preferably, in the sequences (P1) to (P3), the porosity-enhancing powder has a particle size of 0.5-20 μm, and the applied ceramic material powder is fired at a temperature of about 700° C. to 1,300° C., except for the portion subject to simultaneous firing.

The preferred manufacturing method of the present invention involves two stages of firing. A lower-layer portion (a bottom layer) of the porous protective layer and the prismatic laminate are formed through simultaneous firing (first firing step) such that the lower-layer portion covers a longitudinally extending edge portion of the prismatic laminate. A ceramic powder is again applied to the lower-layer portion, followed by the second firing step (C5). According to this method, the lower-layer portion of the porous protective layer is very firmly fixed to an edge portion of the prismatic laminate through simultaneous firing; and an upper-layer portion (a surface layer) of the porous protective layer is firmly fixed to the lower-layer portion through another firing operation. As a result, a water-induced-shock resistant, exfoliation resistant porous protective layer including at least two layers is obtained. Of course, a third firing step may be added; specifically, a paste including a ceramic powder is applied to the fired porous protective layer, followed by firing. When simultaneous firing is not employed in formation of the prismatic laminate and the porous protective layer, the third firing step is employed in order to form, on an edge portion of the laminate, a porous protective layer including at least two layers of different properties. Herein, an applied powder means a paste formed from an appropriate mixture of a ceramic powder, and a carbon powder and/or an organic material powder.

Herein, in most cases, a longitudinally extending edge portion of the prismatic laminate is of an alumina layer, of a solid electrolyte layer of zirconia, of an electrode for use in a sensor cell, or of an electrode-protecting layer for protecting the electrode.

DETAILED DESCRIPTION OF THE INVENTION

Figure 1:
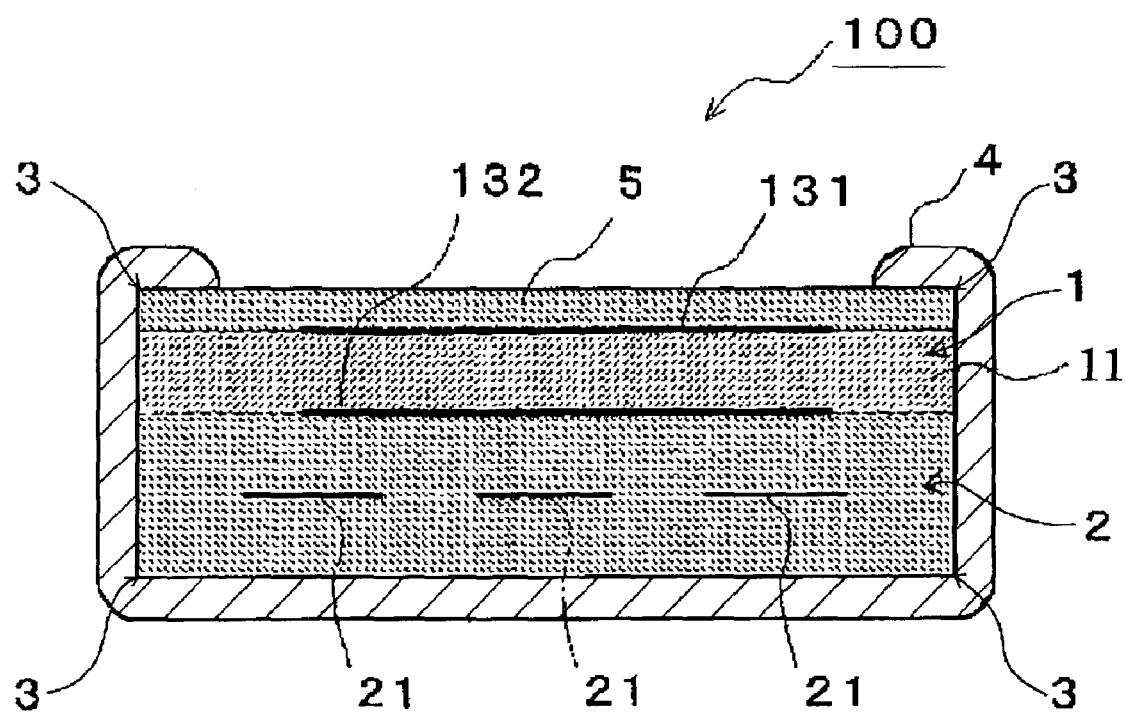
FIG. 1 is a schematic cross-sectional view showing a prismatic gas sensor element according to the present invention.

The present invention will next be described in further detail. However, the present invention should not be construed as being limited thereto.

The present invention provides a prismatic ceramic heater and a prismatic gas sensor element in a multilayered structure including the prismatic ceramic heater, for use in a gas sensor. The prismatic ceramic heater and the prismatic gas sensor element assume a multilayered structure of a substantially rectangular cross section including at least a ceramic heater substrate in which a heating resistor is embedded. A porous protective layer having a porosity of 15%-65% and a thickness of 20-500 μm is formed on a longitudinally extending edge portion (corresponding to a corner of a cross section) of the ceramic heater or of the gas sensor element. The prismatic ceramic heater is generally manufactured by the steps of sandwiching a printed pattern of a heating resistor of Pt, Pd, Ru, W, or the like between two green ceramic layers of alumina, spinel, mullite, or the like, and simultaneously sintering the united members. When a heating resistor of Pt is used in a ceramic heater which is, in turn, used for activating a gas sensor exposed to high-temperature exhaust gas emitted from an internal combustion engine of an automobile, the heating resistor deteriorates due to migration of metal ions present in ceramic. Therefore, preferably, in order to prevent such migration of metal ions, an ion-migration-preventing electrode (a conductor for retaining ionized elements) is embedded in the ceramic together with the heating resistor.

The multilayered gas sensor element of the present invention includes a prismatic laminate having four corners, each having an about 90 degrees as observed on a cross section. The laminate assumes a multilayered structure including a ceramic heater having a heating resistor embedded therein and a "detection layer." The detection layer is constituted by at least a single solid electrolyte layer which partially constitutes an electrochemical cell. A porous protective layer is formed on each of longitudinally extending edge portions of the gas sensor element.

The detection layer constitutes an oxygen sensor cell, which includes an electrode formed on its surface and an electrode-protecting layer for protecting the electrode. The laminate may assume a multilayered structure such that a spacer of an insulating ceramic such as alumina is interposed between a plurality of solid electrolyte layers of zirconia or the like so as to form a gas diffusion space between cell electrodes. The detection layer is usually formed on the ceramic heater substrate directly or via another element and has a pair of electrodes formed on its surface. The detection layer may assume the form of a plate (having a thickness not less than 50 μm) or the form of a thin film (having a thickness less than 50 μm). No particular limitation is imposed on the surface shape of the detection layer. For example, when the gas sensor element of the present invention is to be used as an oxygen sensor, an oxygen-ion-conductive solid electrolyte layer can be used as the detection layer. The solid electrolyte layer can be of any material, so long as the material is oxygen-ion-conductive. Examples of such material include a sintered $Y_2O_3$—$ZrO_2$-based material containing yttria as a stabilizer, a sintered $LaGaO_3$-based material, and a hafnium-containing sintered $Y_2O_3$—$ZrO_2$-based or $LaGaO_3$-based material. Preferably, the solid electrolyte layer contains high-purity alumina in an amount of up to 70% by weight (preferably about 10%-70% by weight). Through employment of such alumina content, the solid electrolyte layer and the alumina ceramic heater substrate including an embedded heating resistor can be strongly joined together through simultaneous sintering.

No particular limitation is imposed on the above-mentioned "electrode," so long as the electrode is electrically conductive. Preferably, the electrode contains at least one of Au, Ag, Ru, Rh, Pd, Ir, Pt, and a like metal. Among these metals, Pt is most preferred in that Pt is unlikely to be oxidized, does not diffuse into the detection layer, has a high melting point, and exhibits good reaction in the 3-layer interface among oxygen, the solid electrolyte, and the electrode. The electrode may contain an oxide such as $ZrO_2$, so long as physical properties of the electrode are not considerably influenced.

In the present invention, a porous protective layer (hereinafter may be referred to as merely a "protective layer") is formed on at least a longitudinally extending edge portion (hereinafter may be referred to as merely an "edge") of a prismatic ceramic heater or gas sensor element. Herein, a "longitudinally extending edge portion" includes a ridge where one of longitudinally extending front and back surfaces (upper and lower surfaces) of a prismatic or platelike ceramic heater or gas sensor element and one of longitudinally extending opposite side surfaces of the heater or element join at an angle of about 90 degrees. Notably, an edge portion that joins one of the front and back surfaces and one of the opposite side surfaces is not limited to a linear portion (i.e., a ridge), but includes a curved portion that joins the two surfaces by means of, for example, a rounded surface.

A protective layer may be formed on a distal-end portion of a prismatic ceramic heater or gas sensor element which is located at a measurement portion to be exposed to a gas to be measured, in such a manner as to cover only a longitudinally extending edge portion, or in such a manner as to cover an edge portion as well as the surface of a portion other than the edge portion (e.g., the entire outer surface, or an outer surface of the distal-end portion which is to be exposed to a gas to be measured). The term "prismatic" means that when the ceramic heater or gas sensor element is cut perpendicularly with respect to its length direction, the resultant cross section assumes a substantially rectangular shape having four corner portions. In view of the mounting position of the ceramic heater or gas sensor element within a gas sensor, among these four edge portions, one or more edge portions which are susceptible to contact with condensed water are selected and covered with the protective layer, thereby yielding an effect of preventing breakage of the ceramic heater or gas sensor element body which could otherwise result from contact with water. More preferably, the protective layer is formed in such a manner as to cover, among longitudinally extending edge portions which are to be directly exposed to a gas to be measured, at least two edge portions; specifically, an edge portion located closest to the heating resistor, and an edge portion located next closest to the heating resistor.

The thickness of the protective layer is not less than 20 μm, preferably not less than 30 μm, more preferably not less than 50 μm, and is not greater than 500 μm, as measured at least an edge portion. In the case where the thickness is less than 20 μm, the protective layer fails to prevent cracking of the ceramic heater or gas sensor element upon contact with water. Notably, the phrase "the protective layer has a thickness not less than 20 μm as measured from an edge portion" means that, in the above-mentioned cross section, an imaginary circle having a diameter of 20 μm can be drawn between an edge portion and the surface of the protective layer.

As described above, by means of forming a protective layer on at least a distal-end portion of a prismatic element having a substantially rectangular cross section which is to be exposed to a gas to be measured, in such a manner as to cover at least one of longitudinally extending edge portions of the element, direct contact or adhesion of a water droplet or the like to the edge portion can be prevented. The thus-formed protective layer buffers transmission of an abrupt thermal shock to an edge portion of the ceramic heater or gas sensor element, thereby preventing fracture of the edge portion which could otherwise result from the thermal shock. A water droplet adhering to the protective layer slowly permeates, while dispersing, through a number of fine holes (pores) in the protective layer. Thus, the water droplet is dispersed or evaporated by ambient heat before reaching the edge portion covered with the protective layer. As a result, a temperature gradient arising in the ceramic heater or gas sensor element is reduced, thereby suppressing cracking or fracture which could otherwise result from thermal shock.

Imparting a porosity of 15%-65% to the protective layer is important. When the porosity is less than 15%, the protective layer may exhibit a deterioration in its function of allowing a water droplet to slowly permeate while dispersing. In the case where the porosity is in excess of 65%, when water adheres to the protective layer, the amount of water passing through the protective layer increases; consequently, the prismatic ceramic heater or gas sensor element may fail to be sufficiently protected. The porosity is preferably 30%-60%, more preferably 40%-55%. Employment of a porosity falling within the preferred range accelerates dispersion of an adhering water droplet to thereby uniformize temperature within the protective layer. Therefore, even when a large amount of water adheres to the protective layer, the protective layer effectively exhibits its thermal-shock-mitigating capability. In the case of a protective layer having a porosity in excess of 60%, in order to protect the prismatic ceramic heater or gas sensor element from thermal shock induced by contact with a large water droplet, the thickness of the protective layer is set to a value near the upper limit, and the average grain size is changed between the surface layer portion and the bottom layer portion.

No particular limitation is imposed on material used to form the above-described protective layer. However, spinel, alumina, mullite, and the like are preferred, since these materials allow relatively easy formation of a porous sintered body of ceramic. Spinel and alumina are particularly preferred. In order to more reliably impart the above-mentioned porosity to the porous protective layer, the porous protective layer may be formed by the steps of adding an organic additive (e.g., carbon, sawdust, a sublimating organic substance such as wax, or a like substance which burns out at the time of firing) for forming pores to an inorganic ceramic powder formed predominantly from spinel or alumina (not less than 70% by weight); forming the resultant mixture into a sheet or paste; and applying the resultant porous-protective-layer-forming material assuming the form of a sheet or paste to a ceramic heater or gas sensor element. When a porous protective layer is formed through thermal spraying as have been practiced conventionally, ceramic particles are tightly joined (the resultant porous protective layer exhibits high density). Thus, the porous protective layer poorly exhibits the effect of buffering transmission of thermal shock induced by contact with water and is thus inferior in water-induced-shock resistance to the porous protective layer formed through firing according to the present invention. Porosity can be increased by means of varying thermal spraying conditions. However, since accurately controlling porosity variations and the thermal spraying position is difficult, thermal spraying is not suitable for actual production of ceramic heaters or gas sensor elements according to the present invention. Particularly, in manufacture of a multilayered gas sensor element, thermal spraying involves a problem in that a thermally sprayed layer is also formed on the electrode-protecting layer; as a result, sensor functions are impaired; for example, sensor response slows down.

The prismatic ceramic heater for heating a gas sensor element, and a prismatic gas sensor element according to the present invention each include an insulating-ceramic element having a heating resistor embedded therein and an electricity application terminal portion for applying electricity to the heating resistor, and are configured such that, in a longitudinally extending edge portion, part of the edge portion located in the vicinity of the heating resistor is coated with a porous protective layer. In order to effectively heat a gas sensor element, the insulating-ceramic element must exhibit excellent thermal conductivity as well as excellent heat resistance and mechanical strength. In order to meet the requirement, the insulating-ceramic element preferably assumes the following composition: main component: alumina ($Al_2O_3$) (not less than 70% by weight, preferably 90%-100% by mass, more preferably 95%-100% by mass); and balance: inorganic binder such as silica ($SiO_2$), magnesia (MgO), or calcia (CaO), and grain-growth inhibitor such as zirconia ($ZrO_2$). When the alumina content is less than 70% by mass, the insulating-ceramic element fails to sufficiently exhibit both insulating property and heat resistance.

Preferably, the insulating-ceramic element having the heating resistor embedded therein excludes, to the greatest possible extent, an alkali metal (particularly, Li, Na, or K) and an alkali earth metal (particularly, Mg, Ca, or Ba). When too much of these metals are included, alkali metal ions and alkali earth metal ions migrate at the time of operation of the heating resistor, as will be described later. Such migrating metal ions cause the heating resistor to thin or break. When an ion-migration-preventing electrode, which will be described later, is not to be embedded together with the heating resistor, the insulating-ceramic element preferably contains alkali metals and alkali earth metals such that 100% by mass of insulating ceramic contains such metals as reduced to their oxides in a total amount not greater than 1% by mass (more preferably not greater than 0.1% by weight).

The above-mentioned "heating resistor" generates heat when electrical current is applied thereto, and is formed within the insulating-ceramic element. The heating resistor usually includes a heating portion and a lead portion. The heating portion generates heat when electrical current is applied thereto. The lead portion leads electrical current applied from an external circuit to the heating portion and hardly generates heat. Usually, the line width of the heating portion is narrower than that of the lead portion and is embedded in the insulating-ceramic element in a meandering form so that the heating portion is longer than the lead portion. The lead portion is embedded in the insulating-ceramic element in the vicinity of a peripheral portion of the insulating-ceramic element in an unmeandering form (e.g., in a shape resembling the letter U). The meandering portion of the heating resistor is formed at a position corresponding to the position of an electrode portion disposed in the vicinity of a distal end portion of the gas sensor element to be exposed to exhaust gas.

No particular limitation is imposed on a material used to form the heating resistor. However, a noble metal is preferred, since firing can be performed in an oxygen atmosphere. Particularly, the heating resistor is formed predominantly from Pt. Further, the heating resistor may contain 5%-20% by mass rhodium. The heating resistor which contains rhodium can quicken start-up of the gas sensor element by virtue of reduced resistance temperature coefficient.

A material used to form the heating resistor may contain a ceramic in addition to a predominant amount of a noble metal. Preferably, in order to attain enhanced adhesion, the ceramic is preferably the same as that contained predominantly in the insulating-ceramic element in which the heating resistor is to be embedded. The heating resistor is formed by the steps of preparing a slurry or paste of a mixture of a material powder containing the above-mentioned substances, an organometallic material compound (a liquid substance), a binder, a plasticizer, a solvent, and the like; applying the slurry or paste to a green ceramic layer through printing; and drying and then firing the green ceramic layer.

The heating resistor is connected to ceramic-heater-electrical current-application terminals provided in or on the insulating-ceramic element and adapted to receive a DC voltage for heating (the terminals provided on the insulating-ceramic element are connected to the heating resistor via through-holes). The ceramic-heater-electrical current-application terminals may be formed from the same material as that used to form the heating resistor, in a manner similar to that for forming the heating resistor.

A conductor for retaining ionized elements can be formed in the insulating-ceramic element. Such conductor is formed on or in an insulating substrate of the ceramic heater and assumes an electric potential equal to or lower than that as measured at the boundary between a heating portion and a lead portion of the heating resistor, thereby preventing a deterioration or breakage of the heating portion of the heating resistor which could otherwise result from metal ions migrating from inside the insulating substrate and from inside a porous protective layer of ceramic. The conductor for retaining ionized elements serves as an ion-migration-preventing electrode.

Oxides of alkali metals, alkali earth metals, and the like contained in the insulating-ceramic element are ionized when the temperature of the heating resistor increases to 700° C. or higher as a result of application of DC voltage to the heating resistor. Such ions migrate to a low-potential portion of the heating resistor and recombine with oxygen at the time of cooling, to thereby form a glass phase. Therefore, the low-potential portion of the heating resistor is apt to deteriorate or break.

When the above-mentioned electric potential is applied to the conductor for retaining ionized elements (ion-migration-preventing electrode), metal ions are attracted thereto rather than to the heating resistor, which is a thin line.

Since a deterioration or breakage of the heating resistor can be prevented as described above, a ceramic heater including the heating resistor and a gas sensor element including the ceramic heater can be each used as a component of an automobile exhaust gas sensor which must exhibit high-temperature durability, and can endure long-term use while maintaining high reliability.

A wiring line for the conductor for retaining ionized elements may be provided independently of that for the heating resistor or may be branched off from the low-potential (negative) lead of the heating resistor. The point is that an electric potential applied to the conductor for retaining ionized elements is lower than that measured at any position on the heating portion of the heating resistor. No particular limitation is imposed on the shape of such conductor; for example, it may be of a linearly extending single pattern or of a meandering single pattern.

The conductor for retaining ionized elements may be disposed on an imaginary plane in or on the insulating substrate, the imaginary plane being different from or the same as that on which the heating resistor is disposed. In the case where the ceramic heater and a solid electrolyte layer used to form a gas sensor cell are to be integrated with each other, the conductor for retaining ionized elements is preferably not disposed between the solid electrolyte layer and the heating resistor. In other words, the conductor for retaining ionized elements is preferably disposed between the heating resistor and a porous protective layer formed on the outer surface of the ceramic heater (the surface on which a gas sensor cell is not overlaid), for the following reason. A new glass phase formed around the ion-detaining conductor as mentioned previously could weaken ceramic strength in the region, possibly causing the heating resistor to become detached from the gas sensor element.

The conductor for retaining ionized elements must be employed when the insulating substrate of the ceramic heater contains an alkali metal element and an alkali earth metal element as reduced to their oxides in a total amount of 1% or more by mass. For example, when the insulating substrate is formed from a typical alumina ceramic which contains as sintering aids 4% by mass silica, 3% by mass magnesia, and 1% by mass calcia, the ion-detaining conductor must be embedded.

No particular limitation is imposed on a material used to form the conductor for retaining ionized elements. However, it may be formed from a material (e.g., Pt) used to form the heating resistor.

A porous protective layer, which is particularly related to the present invention, will be described below. The porous protective layer may comprise a single layer, but preferably comprises two or more layer. Preferably, the properties of the porous protective layer are varied according to an application environment in the following manner: (1) a lower layer and an upper layer differ in porosity; (2) the lower layer and the upper layer differ in porosity or pore diameter; (3) the lower layer and the upper layer differ in main material; and (4) a main material used to form the lower layer and a main material used to form the upper layer differ in average particle size. For example, the upper layer (surface layer) of the porous protective layer serves as a protective layer which functions primarily to provide water-induced-shock resistance, whereas the lower layer (bottom layer) serves as a joining layer for firmly joining the upper layer and a ceramic heater substrate.

The joining layer is formed so as to exhibit an anchor effect for firm fixation to an edge portion of a prismatic laminate to be fired to thereby assume high density. The anchor effect is produced when the joining layer is formed through firing on an edge portion of an alumina ceramic heater or on an edge portion of a ceramic sensor element. The anchor effect is maximized when formed through simultaneous firing. No particular limitation is imposed on the joining layer, so long as it is of a ceramic sintered body. Preferably, the joining layer is of a porous ceramic sintered body of alumina, spinel, mullite, or the like. A porous alumina sintered body is particularly preferred when alumina is used to form a ceramic heater, and zirconia is used to form a solid electrolyte layer, since the porous alumina sintered body exhibits enhanced joining strength in fixation to them through firing. The porous ceramic sintered body may be of a single ceramic or of two or more ceramics. The joining layer is adjusted so as to assume a thickness and a porosity, as measured at an edge portion, that maximize the joining force in terms of fixation to the edge portion. Specifically, the range of adjustment for thickness is 5-100 μm, preferably 10-50 μm, and the range of adjustment for porosity is 15%-65%, preferably 30%-60%.

No particular limitation is imposed on the surface layer of the porous protective layer, so long as the surface layer is of a ceramic sintered body. Preferably, the same material as that used to form the lower layer is used to form the surface layer. Examples of such material include spinel, alumina, and mullite. The ceramic sintered body may be of a single ceramic or of two or more ceramics. The surface layer is adjusted so as to assume a thickness and a porosity, as measured at an edge portion, that maximize water-induced-shock resistance. Specifically, the range of adjustment for thickness is 15-495 μm, preferably 40-400 μm, and the range of adjustment for porosity is 15%-65%, preferably 30%-60%. In the present invention, porosity is defined as the percentage (%) of the area of pores to a unit area as observed on a sufficiently enlarged picture of the cross section of the porous protective layer obtained by use of SEM. Average pore diameter and average grain diameter are also measured by the known methods which use SEM.

The prismatic ceramic heater for heating a gas sensor element of the present invention may be manufactured by any one of the following three methods (a)-(c) according to the present invention:

(a) A porous protective layer is formed on at least a distal-end portion of a prismatic ceramic heater (laminate) which is already fired and assumes high density—the distal-end portion being to be exposed to a gas to be measured—in such a manner that the porous protective layer covers at least one of longitudinally extending edge portions of the ceramic heater body and has a thickness not less than 20 μm as measured from the edge portion.

(b) A green coating layer, which is to become a first porous protective layer, is formed on at least a distal-end portion of a ceramic-heater-forming green laminate which is to be exposed to a gas to be measured, in such a manner as to cover at least one of longitudinally extending edge portions of the green laminate. Subsequently the green coating layer and the green laminate having the green coating layer formed thereon are simultaneously fired so as to fabricate a sintered laminate including the first porous protective layer having a thickness not less than 20 μm.

(c) A green coating layer, which is to become a first porous protective layer, is formed on at least a distal-end portion of a ceramic-heater-forming green laminate which is to be exposed to a gas to be measured, in such a manner as to cover at least one of longitudinally extending edge portions of the green laminate. Subsequently the green coating layer and the green laminate having the green coating layer formed thereon are simultaneously fired so as to fabricate a sintered laminate including the first porous protective layer. Then, a second porous protective layer is formed on the thus-fired first porous protective layer such that a total thickness of the first porous protective layer and the second porous protective layer is not less than 20 μm.

In the above-described method (a) of the present invention, no particular limitation is imposed on the method for forming the porous protective layer. For example, (1) a ceramic powder may be thermally sprayed onto the fired ceramic heater body, (2) a paste or slurry formed from the ceramic powder may be applied to the fired ceramic heater body, followed by firing (heat treatment), or (3) a green sheet formed from the ceramic powder is affixed to the fired ceramic heater body, followed by firing. Method (2) is particularly preferred, since as mentioned previously a porosity falling within the range of the present invention can be readily attained. No particular limitation is imposed on the application method. For example, the paste or slurry may be applied by means of printing, immersion, or brushing. When printing or immersion is to be used to form the coating layer, a paste prepared by mixing a ceramic material powder (e.g., an alumina powder) with a solvent such as acetone or toluene and a binder such as polyvinyl butyral or CMC is preferably used. Solvents may be used singly or in combination, and binders may be used singly or in combination. Preferably, in order to obtain a porous protective layer having an appropriate porosity through firing, a porosity-enhancing agent such as a theobromine powder or a carbon powder is added to the paste. The porosity-enhancing agent powder has a particle size of 2-50 μm, preferably 5-30 μm. In any case, the point is that an edge portion of the sintered laminate obtained through firing or heat treatment is reliably covered with a porous protective layer having a thickness not less than 20 μm.

The ceramic heater substrate is formed from a ceramic green sheet, which in turn is formed from a paste that is prepared by mixing a ceramic material powder and an organic binder such as polyvinyl butyral. Notably, a heating layer is incorporated in the following manner. Two or more ceramic green sheets each containing a predominant amount of insulating ceramic such as alumina are prepared. A heating-layer-forming conductor pattern (film) is formed on the surface of one of the two or more ceramic green sheets. Subsequently, the two or more ceramic green sheets are arranged in layers such that the heating-layer-forming conductor pattern is sandwiched therebetween. Alternatively, a green insulating layer is printed on a ceramic green sheet containing a predominant amount of solid electrolyte such as zirconia. Then, a heating-layer-forming conductor pattern (film) is formed on the green insulating layer.

In the method (b) of the present invention, the above-mentioned coating layer can be formed by use of an ordinary method for forming a film of a metal oxide or a composite oxide. However, the coating layer can be formed by means of, for example, printing, transfer, immersion, or affixment of a green sheet. Among these methods for forming the coating layer, printing, immersion, and affixment of a green sheet involve no particular limitation on firing conditions for simultaneous firing of a green laminate and a coating layer, which is formed on the green laminate by means of printing, immersion, or attachment of a green sheet. However, preferably, the simultaneous firing process is performed at 1,350° C. to 1,600° C. for 1-4 hours. When the coating layer is to be formed by printing or immersion, preferably, the above-described method (a) is complied with. The coating layer described in the above-described methods (a) and (b) may be of two or more layers formed by repeating the described method. Different properties may be imparted as appropriate to the two or more layers.

In the method (c) of the present invention, the second porous protective layer (hereinafter called the "second protective layer") is formed on the first protective layer of the sintered laminate, thereby forming a protective layer consisting of a joining layer and a surface layer. In the present method, the first protective layer functions as the above-mentioned joining layer, and the second protective layer functions as the above-mentioned surface layer. The first protective layer is formed as described above in the method (b) of the present invention. The second protective layer can be formed on at least the first protective layer of the sintered laminate by means of, for example, printing, immersion, or thermal spraying. Notably, when, among these methods for forming the coating layer, printing or immersion is to be used to form the second protective layer, the second protective layer having a target porosity can be formed by the steps of forming a second green coating layer on at least the first protective layer of the sintered laminate, and subjecting the resultant laminate to heat treatment. Preferably, this heat treatment is performed at 700° C. to 1,300° C. for 1-4 hours. Also, in this case, the point is that the coating layer is formed such that a total thickness of the first protective layer and the second protective layer is not less than 20 μm.

The prismatic gas sensor element of the present invention may be manufactured by any one of the following three methods (d)-(f) according to the present invention:

(d) A porous protective layer is formed on at least a distal-end portion of a predetermined element body which is already fired and assumes high density—the distal-end portion being to be exposed to a gas to be measured—in such a manner that the porous protective layer covers at least one of longitudinally extending edge portions of the element body and has a thickness not less than 20 μm as measured from the edge portion.

(e) A prismatic green laminate is formed by overlaying, onto the ceramic-heater-substrate-forming green sheet, a detection-layer-forming green sheet or paste having a pair of green electrode patterns formed thereon, and an electrode-protecting-layer-forming green sheet or paste for converting the electrodes. A green coating layer, which is to become a first porous protective layer, is formed on at least a distal-end portion of the prismatic green laminate which is to be exposed to a gas to be measured, in such a manner as to cover at least one of longitudinally extending edge portions of the green laminate. Subsequently the green coating layer and the green laminate having the green coating layer formed thereon are simultaneously fired so as to fabricate a sintered laminate including the first porous protective layer having a thickness not less than 20 μm.

(f) A prismatic green laminate is formed by overlaying, onto the ceramic-heater-substrate-forming green sheet, a detection-layer-forming green sheet or paste having a pair of green electrode patterns formed thereon, and an electrode-protecting-layer-forming green sheet or paste for converting the electrodes. A green coating layer, which is to become a first porous protective layer, is formed on at least a distal-end portion of the green laminate which is to be exposed to a gas to be measured, in such a manner as to cover at least one of longitudinally extending edge portions of the green laminate. Subsequently the green coating layer and the green laminate having the green coating layer formed thereon are simultaneously fired so as to fabricate a sintered laminate having the first porous protective layer formed thereon. Then, a second porous protective layer is formed on the thus-fired first porous protective layer such that a total thickness of the first porous protective layer and the second porous protective layer is not less than 20 μm.

In the above-described method (d) of the present invention, no particular limitation is imposed on the method for forming the porous protective layer. The porous protective layer is formed on the fired element body in a manner similar to that of the method (a) of the present invention. In order to enhance joining strength, a ceramic (powder) which is the same as or similar to that used to form the element body is preferably used to form the porous protective layer. Notably, the method (d) of the present invention is specifically carried out in the following manner. A prismatic green laminate is formed by overlaying, onto the ceramic-heater-substrate-forming green sheet, a detection-layer-forming green sheet or paste having a pair of green electrode patterns formed thereon, and an electrode-protecting-layer-forming green sheet or paste for converting the electrodes. The prismatic green laminate is fired. A distal-end portion of the resultant sintered laminate which is to be exposed to a gas to be measured is immersed in a slurry used to form a porous protective layer, thereby forming a coating layer on the distal-end portion, including edge portions, of the sintered laminate. The thus-prepared sintered laminate is subjected to heat treatment to thereby form the porous protective layer having a thickness not less than 20 μm.

In the above-describe method (e) of the present invention, the "ceramic-heater-substrate-forming green sheet" is a ceramic green sheet which is fired to become a ceramic heater substrate. The ceramic green sheet is formed from a paste that is prepared by mixing a ceramic material powder and an organic binder such as polyvinyl butyral. Notably, a heating layer is incorporated in the following manner. Two or more ceramic green sheets each containing a predominant amount of insulating ceramic such as alumina are prepared. A heating-layer-forming conductor pattern (film) is formed on the surface of one of the two or more ceramic green sheets. Subsequently, the two or more ceramic green sheets are layered such that the heating-layer-forming conductor pattern is sandwiched therebetween. Alternatively, a green insulating layer is printed on a ceramic green sheet containing a predominant amount of solid electrolyte such as zirconia. Then, a heating-layer-forming conductor pattern (film) is formed on the green insulating layer.

The above-mentioned "detection-layer-forming green sheet or detection-layer-forming paste" is a green sheet which is fired to become a detection layer, and is fabricated in the following manner. A powder of zirconia solid solution which contains a stabilizer such as yttria or calcia is mixed with an organic binder such as polyvinyl butyral, thereby forming a paste. The paste is used to prepare a detection-layer-forming green sheet or a detection-layer-forming paste. A conductive paste which contains platinum or a platinum alloy as a main component is applied, in a predetermined pattern through printing, to a predetermined region of the detection-layer-forming green sheet, or to a predetermined region of the detection-layer-forming paste applied (printed) onto a substrate-forming green sheet, followed by drying. In this manner, a pair of electrodes (a detection electrode and a reference electrode) are formed. When the detection-layer-forming green sheet or the detection-layer-forming paste differs from the substrate-forming green sheet in terms of a main component, the detection-layer-forming green sheet or the detection-layer-forming paste preferably contains the same ceramic component as that contained predominantly in the substrate-forming green sheet. For example, when a detection layer is to be laminated on a substrate configured such that a heating resistor is sandwiched between two ceramic sheets each containing a predominant amount of alumina, alumina—which is the main component of the substrate-forming green sheet—is contained in a detection-layer-forming green sheet or a detection-layer-forming paste, both of which contain zirconia.

The above-mentioned "electrode-protecting-layer-forming green sheet or electrode-protecting-layer-forming paste"

is a green sheet or a paste which is fired to become a porous electrode-protecting layer, and is fabricated in the following manner. A ceramic powder (e.g., a powder of partially stabilized zirconia (containing yttria, calcia, or the like), spinel, or alumina, a powder of their mixture, or a powder of their compound, a porosity-enhancing agent (e.g., carbon, sawdust, or wax), and an organic binder such as polyvinyl butyral are mixed, thereby forming a paste. The paste is used to prepare an electrode-protecting-layer-forming green sheet or electrode-protecting-layer-forming paste. The green sheet or paste is applied onto a predetermined region of the detection layer in such a manner as to cover the electrode (detecting electrode), followed by drying. The paste is applied through printing. The porosity-enhancing agent burns out at the time of firing or heat treatment, thereby forming pores within the electrode-protecting layer.

The above-described method (f) of the present invention is similar to the above-described method (c) of the present invention in terms of formation of the porous protective layer. In the method (f), the "ceramic-heater-substrate-forming green sheet," "detection-layer-forming green sheet or detection-layer-forming paste," and "electrode-protecting-layer-forming green sheet or electrode-protecting-layer-forming paste" are as defined above. The method (f) is carried out, for example, in the following manner. A prismatic green laminate is formed by overlaying, onto the ceramic-heater-substrate-forming green sheet, a detection-layer-forming green sheet or paste having a pair of green electrode patterns formed thereon, and an electrode-protecting-layer-forming green sheet or paste for converting the electrodes. A green coating layer (to be formed from a mixed paste of a carbon powder, an alumina ceramic powder, and an organic binder), which is to become a first porous protective layer, is formed through printing on at least a distal-end portion of the green laminate which is to be exposed to a gas to be measured, in such a manner as to cover at least one of longitudinally extending edge portions of the green laminate, followed by drying. Subsequently the dried green laminate having the green coating layer formed thereon is fired at 1,350° C. to 1,600° C. for 1-4 hours, thereby obtaining a sintered laminate including the first porous protective layer formed on edge portions of the laminate through simultaneous firing. Then, the distal-end portion of the resultant sintered laminate which is to be exposed to a gas to be measured is immersed in a slurry consisting of a spinel powder and water and is then subjected to drying, thereby forming a second green coating layer of spinel powder in such a manner as to cover the first porous protective layer formed on the edge portions of the sintered laminate. Subsequently, the resultant laminate is fired or heat-treated at a temperature (700° C. to 1,300° C.) lower than that for simultaneous firing for 1-4 hours, thereby forming the porous protective layer such that the total thickness of the first and second porous protective layers is not less than 20 μm.

DESCRIPTION OF THE PREFERRED EMBODIMENTS

1-1. Configuration of Multilayered Gas Sensor Element

Figure 2:
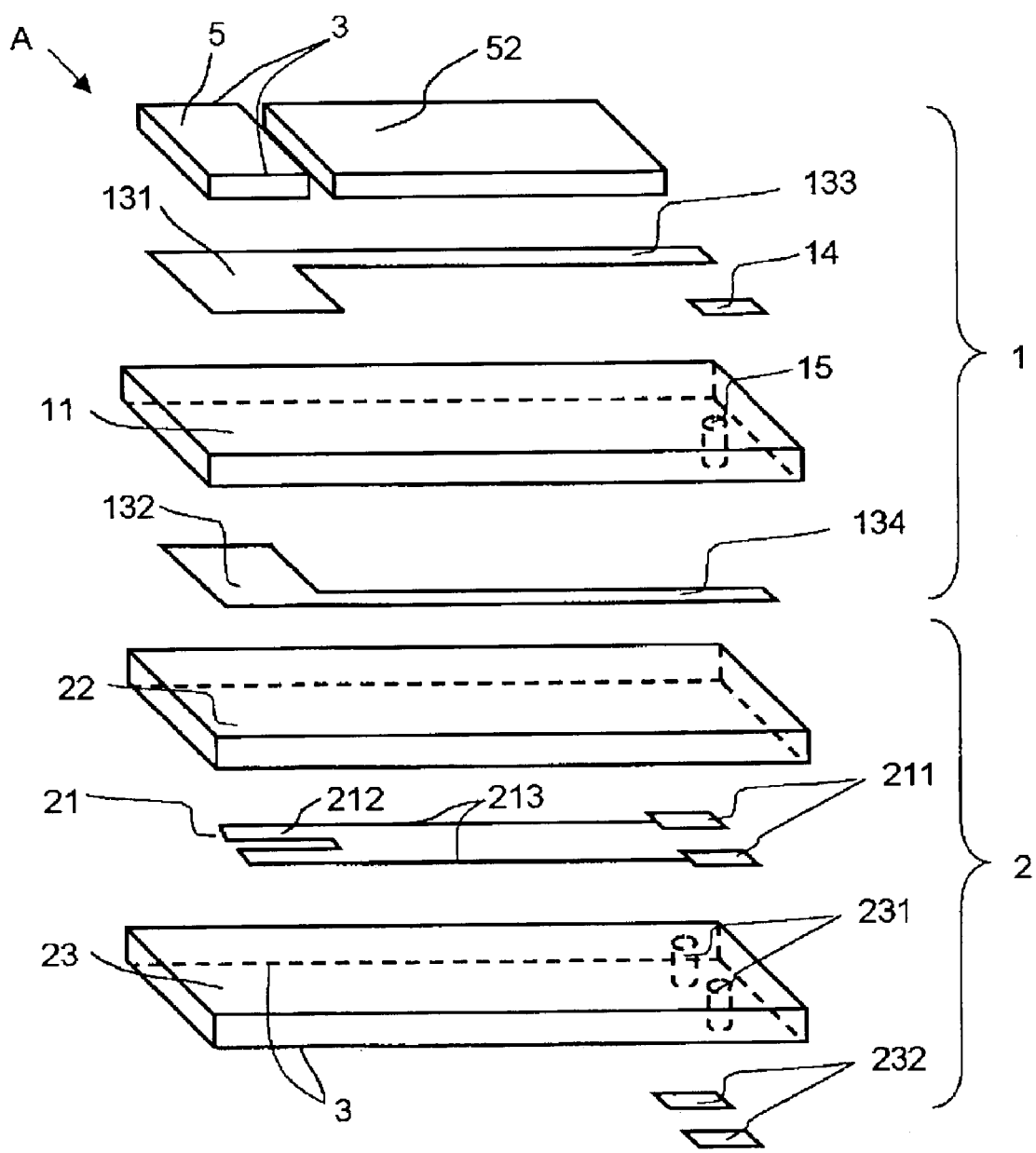
FIG. 2 is an exploded perspective view showing the internal structure of the gas sensor element of FIG. 1.

A prismatic gas sensor element 100 will be described with reference to FIGS. 1 and 2. FIG. 1 shows a cross section of a prismatic oxygen sensor element 100 in accordance with the present invention. As shown in FIG. 1, the prismatic oxygen sensor element 100 has a rectangular cross section having four corners (corresponding to longitudinally extending edge portions 3 of FIG. 2) of about 90 degrees. FIG. 2 is an exploded perspective view showing the internal structure of the prismatic gas sensor element 100 of FIG. 1, excluding a porous protective layer 4. FIG. 2 shows a prismatic multilayered element in a multilayered structure including an oxygen sensor cell 1 and a prismatic ceramic heater 2 for heating the oxygen sensor cell 1. The oxygen sensor cell 1 and the prismatic ceramic heater 2 are joined together through simultaneous firing.

In FIG. 2, the oxygen sensor cell 1 includes an oxygen-ion-conductive solid electrolyte layer 11 of zirconia, an oxygen-detecting electrode 131, an oxygen-reference electrode 132, and leads 133 and 134. The oxygen-ion-conductive solid electrolyte layer 11 is sandwiched between the oxygen-detecting electrode 131 and the oxygen-reference electrode 132. The lead 133 extends from the oxygen-detecting electrode 131, whereas the lead 134 extends from the oxygen-reference electrode 132. The electrodes 131 and 132 are disposed in the vicinity of one end of the solid electrolyte layer 11 which is to be exposed to high-temperature exhaust gas. The lead 134 of the reference electrode 132 is electrically connected to an external terminal 14 via a through-hole 15 which extends through the solid electrolyte layer 11 in the vicinity of the other end of the solid electrolyte layer 11, whereby the lead 134 and the lead 133 of the detecting electrode 131 form a pair of external terminals on one side of the solid electrolyte layer 11 for establishing connection to an external circuit. (Notably, the solid electrolyte layer 11 corresponds to the "detection layer" referred to herein.) Generally, the detecting electrode 131 is covered with a porous electrode-protecting layer 5; and the lead 133 of the detecting electrode 131, excluding its external-terminal-connection portion, is covered with a protective reinforcing layer 52, which is adapted to provide gas-tight protecting for the solid electrolyte layer 11.

A ceramic heater 2 includes an inner alumina ceramic layer 22, an outer alumina ceramic layer 23, and a heating resistor 21 sandwiched therebetween. The heating resistor 21 includes a meandering line portion 212 formed predominantly from a noble metal such as platinum and serving as a heating portion and is located at a position substantially corresponding to that of the electrodes 131 and 132. The leads 213 which connect to two end portions 211 of the heating resistor 21 are formed wide and are electrically connected, via corresponding through-holes 231, to corresponding external terminals 232 which are formed on the outer surface of the outer alumina layer 23 and which are to be connected to an external circuit.

The longitudinally extending edge portions 3 of the gas sensor element 100 of a prismatic laminate are two outer edge portions (two lower edge portions in FIG. 2) of the prismatic ceramic heater 2, two edge portions of the electrode-protecting layer 5, and two edge portions of the protective reinforcing layer 52.

As observed on the cross section of FIG. 1 taken across the electrodes 131 and 132 and across the heating resistors 21, the gas sensor element 100 is characterized in that the sharp corners each having about 90 degrees and corresponding to the longitudinally extending four edge portions 3 of the prismatic laminate are covered with the porous protective layer 4 assuming an arcuate outer surface, whereby the sharp corners are eliminated.

Figure 4:
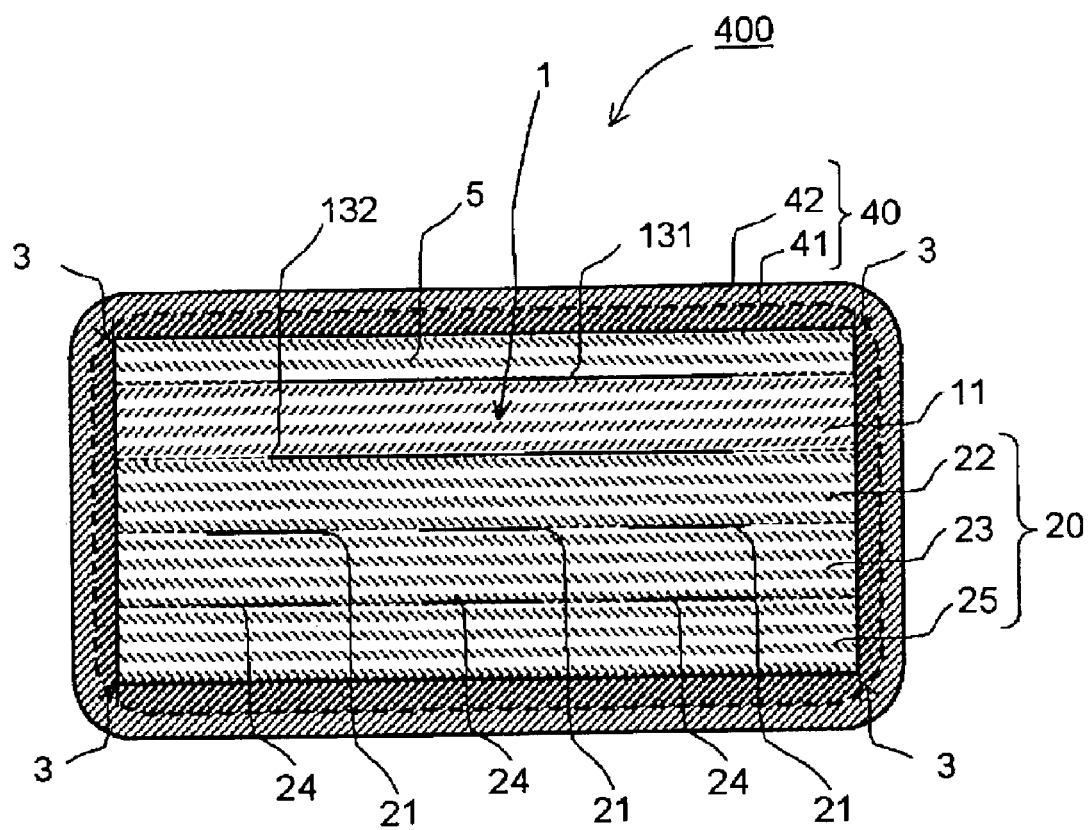
FIG. 4 is a schematic cross-sectional view showing a further prismatic gas sensor element according to the present invention.

The water-induced-shock resistant, porous protective layer 4 covering the edge portion 3 has a minimum thickness of 20 μm, preferably 50 μm, more preferably 100 μm, and has a maximum thickness of about 500 μm. The porous protective layer 40 may extend along the entire circumference of the gas sensor element 400 including the porous electrode-protecting layer 5 as shown in FIG. 4, instead of terminating at the edge portions 3 of the electrode-protecting layer 5 as shown in FIG. 1. The porous protective layer 40 and the electrode-protective layer 5 may be formed from a common material. In any case, the porous protective layer 40 covering an edge portion has a roundly curved outer surface. Specifically, as shown in the cross section of FIG. 1, the porous protective layer 4 covers the edge portion 3 such that the outer surface of the porous protective layer 4 assumes an arcuate curve extending over the edge portion 3, thereby providing homogeneous, consistent water-induced-shock resistance. The radius of the arcuate curve is at least 10 μm, preferably not less than 50 μm, more preferably 100 μm.

The size of the prismatic gas sensor element 100 is variable within the following ranges: length 30-60 mm, width 2.5-6 mm, and thickness 1-3 mm. In the present embodiment, the gas sensor element 100 has a length of 40 mm, a width of 3 mm, and a thickness of 2 mm.

Figure 3:
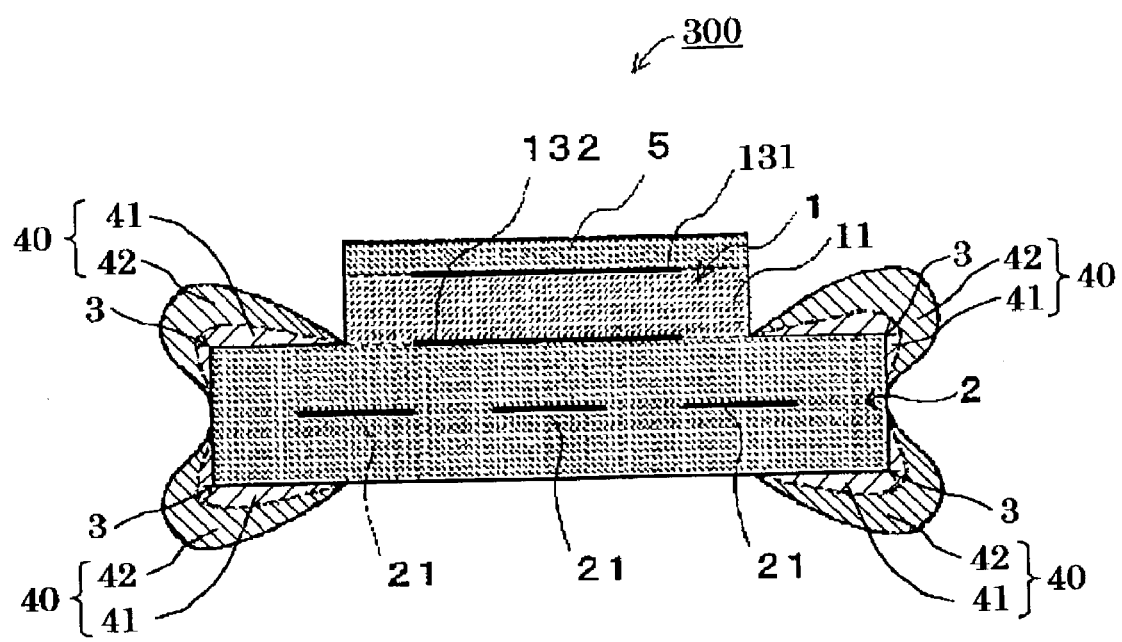
FIG. 3 is a schematic cross-sectional view showing another prismatic gas sensor element according to the present invention.

The cross-sectional shape of the prismatic gas sensor element is not limited to a square or rectangular shape. For example, as shown in the prismatic gas sensor element 300 of FIG. 3, the oxygen sensor cell 1 (detection layer) to be overlaid on the ceramic heater 2 may be narrower than the ceramic heater 2. Also, as shown in FIG. 3, the porous protective layer 40 may be only formed on the edge portions 3 of the oxygen sensor cell 1 and/or the ceramic heater 2. This is because when the separately fabricated oxygen sensor cell 1 and the ceramic heater 2 are joined together, the shape of FIG. 3 may result. In FIG. 3, the porous protective layer 40 is only formed on the edge portions 3 of the ceramic heater 2 for the following reason: the ceramic heater 2 is formed from a material having a thermal conductivity higher than that of zirconia, and the edge portions 3 of the ceramic heater 2 are located closer to the heating resistor 21 than those of the detection layer. When the edge portions 3 of the detection layer are located closer to the heating resistor 21 than those of the ceramic heater 2 or are located in the vicinity of the heating resistor 21, the porous protective layer must be formed on the edge portions 3 of the detection layer (oxygen sensor cell 1).

Figure 5:
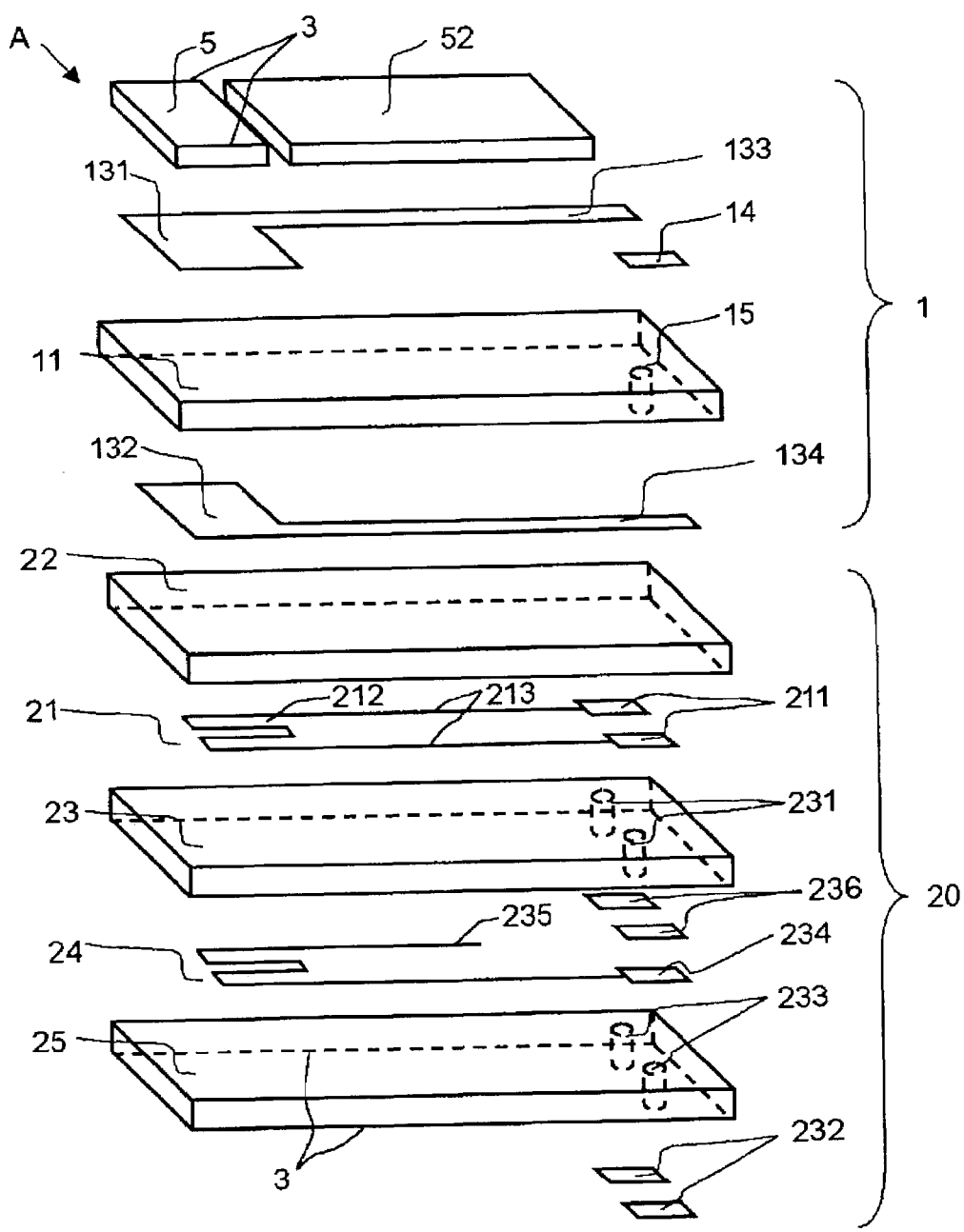
FIG. 5 is an exploded perspective view showing the internal structure of the gas sensor element of FIG. 4.

FIG. 4 is a sectional view of a prismatic gas sensor element 400 according to another embodiment of the present invention. The prismatic gas sensor element 400 is configured such that a third alumina ceramic layer 25 is disposed outside the outer alumina ceramic layer 23 of the prismatic gas sensor element of FIG. 2, an ion-migration-preventing electrode 24 is sandwiched therebetween, and such that the porous protective layer 40 consisting of a joining layer 41 and a surface layer 42 is formed along the entire circumference of the prismatic gas sensor element 400. FIG. 5 is an exploded perspective view showing the internal structure of the prismatic gas sensor element 400 of FIG. 4. Although the lead 235 of the ion-migration-preventing electrode 24 is connected to the negative side of a heating resistor 21, the ion-migration-preventing electrode 24 is preferably disposed between the porous protective layer 41, 42 and the heating resistor 21 and must not be disposed between the heating resistor 21 and the sensor cell 1.

Figure 6:
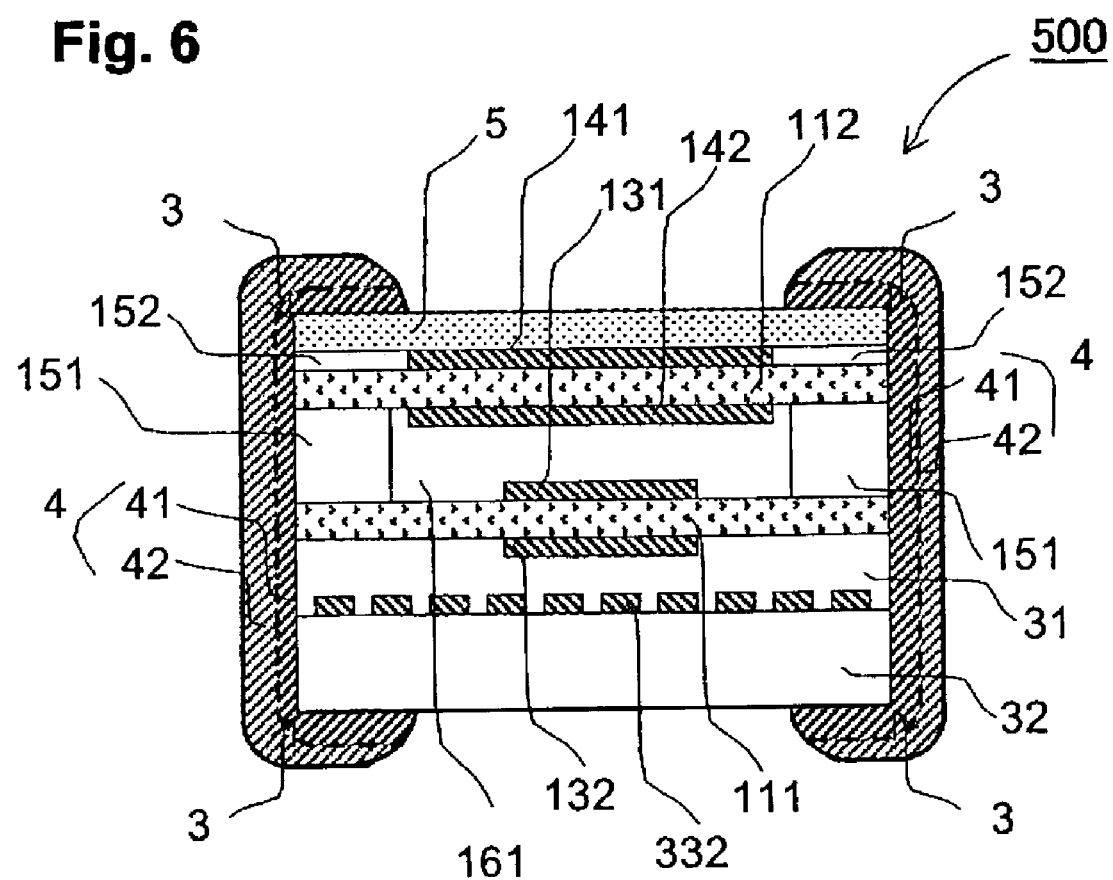
FIG. 6 is a schematic cross-sectional view showing still another prismatic gas sensor element according to the present invention.

The present invention is also applicable to a prismatic gas sensor element in a multilayered structure including a ceramic heater substrate and a plurality of solid electrolyte layers for forming a plurality of cells, such as a full range air/fuel ratio sensor (a so-called universal oxygen sensor) or a $NO_x$ sensor (a nitrogen oxide gas sensor). For example, FIG. 6 is a sectional view of a prismatic gas sensor element 500 of a full range air/fuel ratio sensor. As shown in FIG. 6, heating resistors 332 are sandwiched between two alumina substrates 31 and 32, thereby forming a ceramic heater. On the ceramic heater, a first solid electrolyte layer 111 having a detecting electrode 131 and a reference electrode 132 formed thereon is overlaid. A spacer 161 having a gas diffusion inlet 151 formed therein is overlaid on the first solid electrolyte layer 111, and a second solid electrolyte layer 112 having an outer electrode 141 and an inner electrode 142 formed thereon is overlaid on the spacer 161 such that the inner electrode 142 faces the electrode 131 of the first solid electrolyte layer 111, thereby forming an oxygen-pumping cell. An insulating layer 152 is disposed on the second solid electrolyte layer 112. An electrode-protecting layer 5 is formed on the insulating layer 152 and on the outer electrode 141. Edge portions 3 of the gas sensor element 500 are present on the ceramic heater and on the electrode-protecting layer 5. A porous protective layer 4 of ceramic consisting of a joining layer 41 and a surface layer 42 is formed on the edge portions 3 through firing.

In the prismatic gas sensor elements of FIGS. 3, 4, and 6, the porous protective layer 4 formed on the edge portions 3 consists of the joining layer 41 joined to the edge portions 3 and the surface layer 42 formed on the joining layer 41.

1-2. Configuration of Prismatic Ceramic Heater for Heating Gas Sensor

Figure 7:
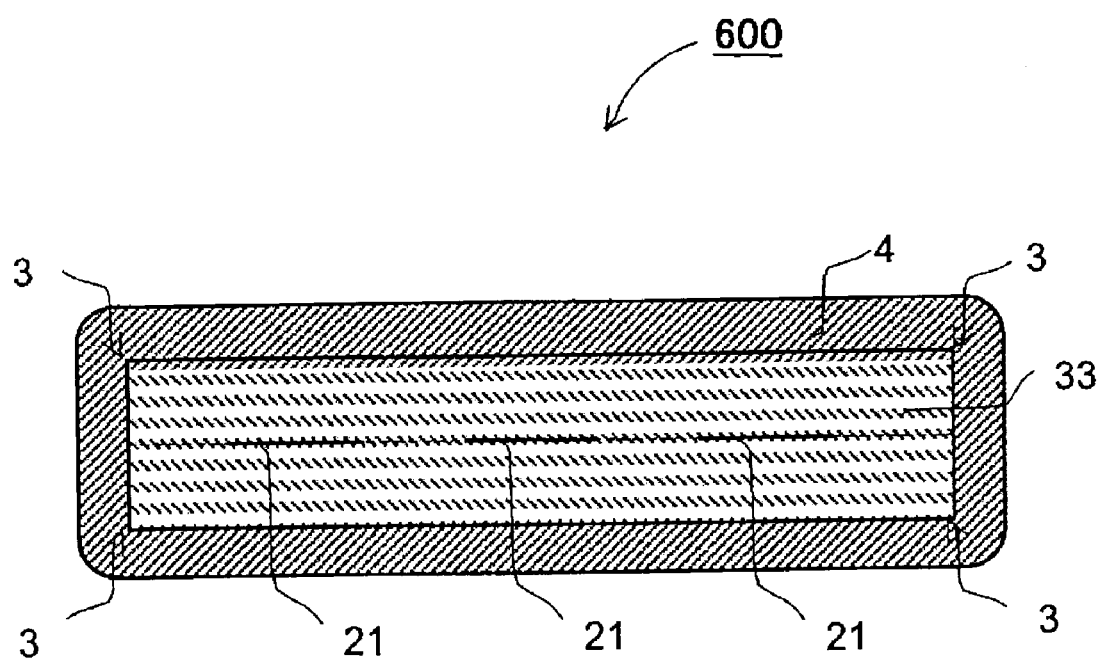
FIG. 7 is a schematic cross-sectional view showing a prismatic ceramic heater according to the present invention.
Figure 8:
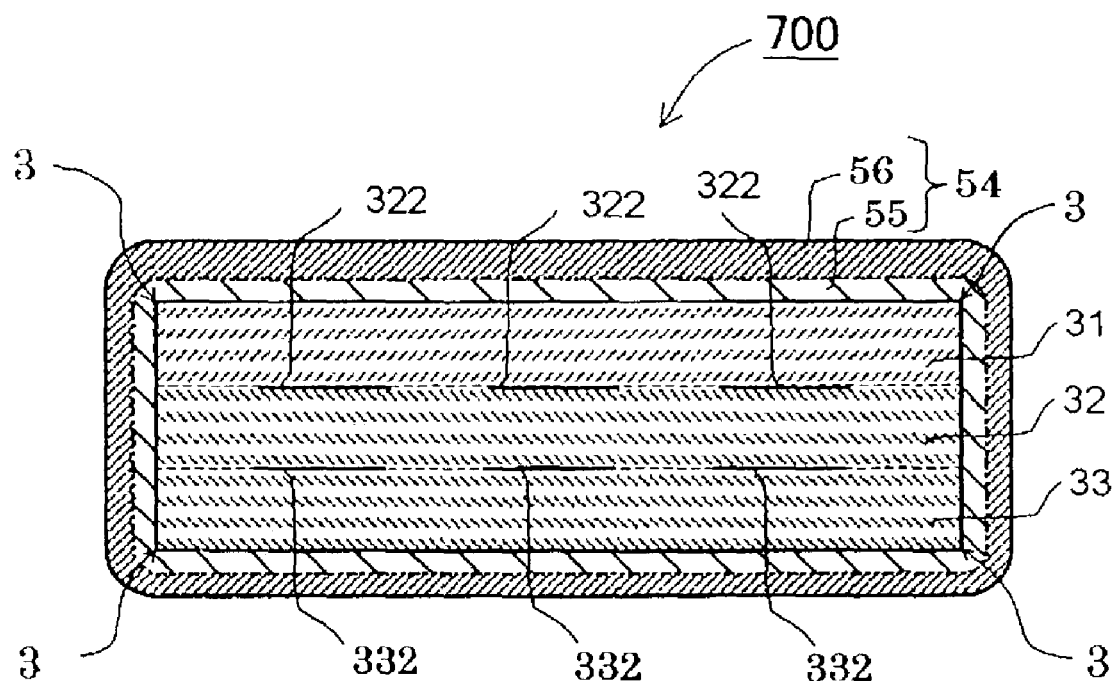
FIG. 8 is a schematic cross-sectional view showing another prismatic ceramic heater according to the present invention.

FIGS. 7 and 8 are sectional views showing two kinds of prismatic ceramic heaters of the present invention for heating a gas sensor, the prismatic ceramic heaters being completed independently of a gas sensor cell.

The prismatic ceramic heaters are configured such that a heating resistor 21 or 332 formed predominantly from platinum is formed in or on a ceramic substrate 33 formed predominantly from alumina (FIGS. 7 and 8). Optionally, a conductor for retaining ionized elements (ion-migration-preventing electrode) 322 is embedded in order to prevent a deterioration or breakage of the heating resistor 332 which could otherwise result from migration of metal ions (FIG. 8). In FIG. 7, the porous protective layer 4 of ceramic is formed on the ceramic heater 600 along the entire circumference of the ceramic heater 600 including the edge portions 3. In the prismatic ceramic heater 700 of FIG. 8, the porous protective layer 54 consists of a joining layer 55 and a surface layer 56.

2. Structure of Gas Sensor

Figure 9:
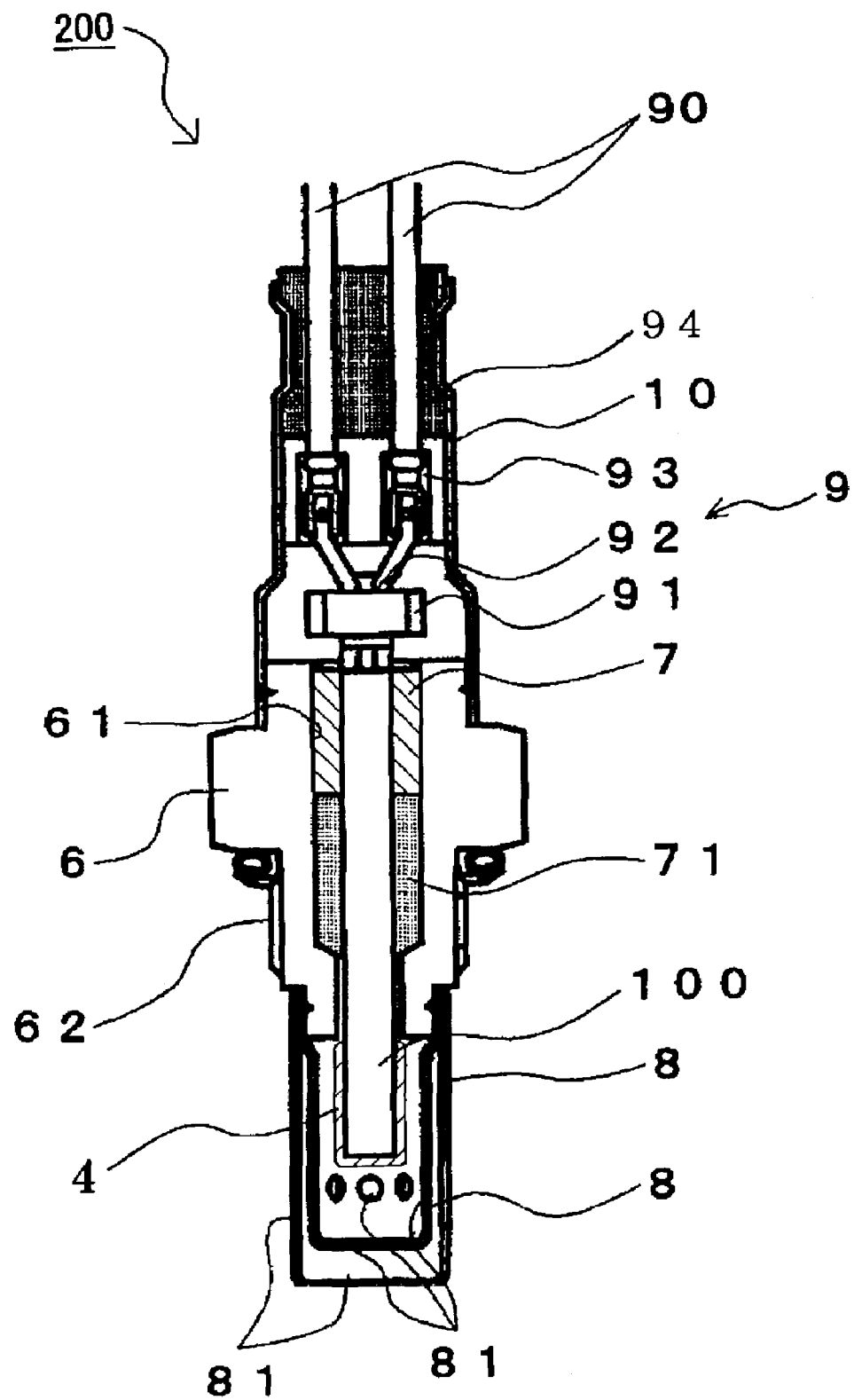
FIG. 9 is a sectional view showing the internal structure of a gas sensor configured such that a prismatic gas sensor element of the present invention is fixedly accommodated in a sensor housing.

FIG. 9 is a sectional view showing the internal structure of an oxygen sensor 200 suited for measuring the oxygen concentration of exhaust gas emitted from an internal combustion engine. The oxygen sensor 200 is configured such that the prismatic gas sensor element 100 of the present invention is firmly fixed in place by means of a sensor housing 9.

The gas sensor element 100 is inserted into a through-hole 61 of a tubular sensor housing body 6 such that an end gas-sensing portion thereof projects from one end of the sensor housing body 6, and is firmly fixed in the sensor housing by means of a sealing glass 7 and a cushion ring 71. Two metallic inner and outer protectors 8 are disposed concentrically at an end portion of the sensor housing body 6 in such a manner as to cover the gas-sensing portion (a projecting portion) of the gas sensor element 100. A number of ventilation holes 81 are formed in the protectors 8 for introducing exhaust gas into the interior of the protectors 8. The other end of the sensor housing body 6 is welded to a sleeve 10. A male-threaded portion 62 is formed on an outer circumferential portion of the sensor housing body 6 and is screwed into, for example, an exhaust pipe of an internal combustion engine. The prismatic gas sensor element 100 is electrically connected to an external circuit via a first connector 91, metallic wires 92, second connectors 93, and lead wires 90 extending through a grommet 94.

In the prismatic gas sensor element 100 of the gas sensor 200, a porous protective layer resistant to water-induced shock is formed on the gas sensing portion, but is not formed on a portion which is not exposed to exhaust gas (a portion which is fixedly attached to the sensor housing body 6), for the following reason: the mechanical strength of the porous protective layer is relatively low, and the portion to be fixedly attached to the sensor housing 6 must exhibit good dimensional accuracy.

3-1. Method for Manufacturing Multilayered Gas Sensor Element (with Single-Layered Porous Protective Layer)

A method of manufacturing a multilayered gas sensor element shown in FIGS. 1 and 2 will be described.

(1) Fabrication of Oxygen-Concentration-Cell-Element-Forming Green Sheet

A powder of zirconia solid solution (100 g) which contained a stabilizer such as yttria or calcia, a alumina powder (100 g), and an organic binder (polyvinyl butyral; 26 g) were mixed, thereby yielding a paste. By use of the paste, a green solid electrolyte sheet (thickness about 100 μm) which was to become the oxygen-concentration-cell-forming solid electrolyte layer 11 and having such a size as to provide five elements was formed. Subsequently, through-holes were formed in the green solid electrolyte sheet at predetermined positions so as to provide through-holes 15 for five elements.

Next, a conductive paste containing a predominant amount of platinum (including the same component as that of the solid electrolyte in an amount of 15% by weight) was applied, in predetermined patterns through printing (thickness about 20 μm), to predetermined regions on the oxygen-concentration-cell-forming solid electrolyte layer 11 (including the through-holes which were to become the through-holes 15), followed by drying, thereby forming conductor patterns (films) which were to become detecting electrodes 131, reference electrodes 132, lead portions 133 and 134, and signal outlet terminals 14. A paste (a mixture of alumina (98 g) and the same component as that of the solid electrolyte (2 g)) used to form a protective reinforcing layer 52 was applied through printing (thickness about 100 μm) to the entire surface—excluding the regions corresponding to the detecting electrodes 131, an end portion 135 of the lead portion 133, and the signal outlet terminal 14—of the oxygen-concentration-cell-forming solid electrolyte layer 11 on which the detecting electrode 131 was formed. Thus was obtained an oxygen-concentration-cell-element-forming green sheet.

(2) Fabrication of First-Substrate-Forming Green Sheet

Next, an alumina powder (100 g) and an organic binder (polyvinyl butyral; 12 g) were mixed, thereby yielding a paste (containing as impurities silica and zirconia in an amount of 2%-10% by weight). By use of the paste, a green alumina sheet (thickness 1.3 mm) which was to become the second substrate layer 23 was formed. Through-holes were formed in the green alumina sheet so as to provide through-holes 231 for five elements. Subsequently, a conductive paste containing a predominant amount of platinum (including the same component as that of the alumina sheet in an amount of 10% by weight) was applied, in predetermined patterns through printing (thickness 25 μm), to predetermined regions on the green alumina sheet which was to become the second substrate layer 23 (including the through-holes which were to become the through-holes 231), followed by drying, thereby forming conductor patterns which were to become heating resistors 21 consisting of a meandering line portion 212 and leads 213 and a pair of ceramic heater electricity application terminals 211. By use of the same paste, conductor patterns which were to become ceramic-heater-electricity-application terminals 232 were printed (thickness 30 μm) on the side of the green sheet opposite that on which the heating resistor 21 was to be formed. The terminals 211 and the corresponding terminals 232 were made to be electrically connected via the through-holes 231. Also, a green alumina sheet (thickness 0.7 mm) which was to become the first substrate layer 22 was fabricated in a manner similar to that for fabrication of the second substrate layer 23. This green alumina sheet which was to become the first substrate layer 22 was overlaid on the green alumina sheet which was to become the second substrate layer 23 such that the conductor pattern which was to become the heating resistor 21 was sandwiched therebetween. The resultant assembly was compression-bonded under reduced pressure, thereby yielding a substrate-forming green sheet which was to become the substrate 2.

(3) Assembly, Debindering, Firing, and Formation of Porous Protective Layer

The oxygen-concentration-cell-element-forming green sheet and the substrate-forming green sheet were stuck together. A protection-layer-forming green sheet (thickness 200 μm) which was to become the electrode protection layer 5 was prepared previously in the following manner: an alumina powder, a carbon powder, a dispersant, and a binder formed from butyral resin and dibutyl phthalate were mixed according to a predetermined composition to thereby form slurry; and by use of the slurry, the protection-layer-forming green sheet was formed. The protection-layer-forming green sheet was laminated on the conductor patterns which were exposed on the oxygen-concentration-cell-element-forming green sheet and were to become the detecting electrodes 131. The resultant assembly was compression-bonded under reduced pressure, thereby yielding a laminate. Thus-obtained laminate was cut into five green laminates, which were to become element bodies A. Subsequently, a paste including an alumina powder (70 g), an organic binder (polyvinyl butyral; 12 g), an organic solvent (butyl carbitol; 25 g), and a porosity-enhancing agent (a carbon powder (particle size 5 μm); 30 g) was applied, through printing, to the green laminates in such a manner as to cover at least four longitudinally extending edge portions 3 of the green laminates and such that the porous protective layer 4 obtained through firing assumed an above-mentioned predetermined thickness of 20 μm, 50 μm, 100 μm, and 200 μm, followed by drying. Next, the green laminates were heated in the atmosphere while heating temperature was raised at a rate of 20° C. per hour, maintained at a maximum temperature of 450° C. for 1 hour so as to be debindered (so as to undergo a debinder process), and then fired at 1500° C. for 1 hour, thereby providing laminate-type gas sensor elements 100 each having the porous protective layer (single layer) 4 formed thereon.

3-2. Method for Manufacturing Ceramic Heater (with Multilayered Porous Protective Layer) for Heating Gas Sensor Element A method of manufacturing a ceramic heater having a multilayered porous protective layer, which corresponds to the heater section 20 of the multilayered gas sensor element shown in FIGS. 4 and 5, will be described.

(1) Fabrication of Green Sheet

An alumina powder (100 g) and an organic binder (polyvinyl butyral; 12 g) were mixed, thereby yielding a paste (containing as impurities silica and zirconia in an amount of 2%-10% by weight). By use of the paste, a green alumina sheet (thickness 1.1 mm) which was to become the third substrate layer 25 was formed. Through-holes were formed in the green alumina sheet so as to provide through-holes 233 for five elements. A conductive paste containing a predominant amount of platinum (including the same component as that of the alumina sheet in an amount of 10% by weight) was applied, in predetermined patterns through printing (thickness 25 μm), to predetermined regions on the green alumina sheet which was to become the third substrate layer 25, followed by drying, thereby forming a conductor pattern which was to become a conductor for retaining ionized elements 24 and a conductor for retaining ionized elements a terminal 234 therefor. Next, by use of the same paste, conductor patterns which were to become ceramic-heater-electricity-application terminals 232 were printed (thickness 30 μm) on the side of the green sheet opposite that on which the conductor for retaining ionized elements 24 was to be formed. The terminal 234 and the corresponding terminal 232 were made to be electrically connected via the corresponding through-holes 233.

Also, a green alumina sheet (thickness 0.7 mm) which was to become a second substrate layer 23 was fabricated in a manner similar to that for fabrication of the third substrate layer 25. Through-holes were formed in the green alumina sheet so as to provide through-holes 231 for five elements. Subsequently, a conductive paste containing a predominant amount of platinum (including the same component as that of the alumina sheet in an amount of 10% by weight) was applied, in predetermined patterns through printing (thickness 25 μm), to predetermined regions on the green alumina sheet which was to become the second substrate layer 23, followed by drying, thereby forming conductor patterns which were to become a heating resistor 21 and pairs of connection electrodes 211. Next, by use of the same paste; conductor patterns which were to become connection electrodes 236 were printed (thickness 30 μm) on the side of the green sheet opposite that on which the heating resistor 21 was to be formed. The electrodes 211 and the electrodes 236 were made to be electrically connected via the through-holes 231.

Next, a green alumina sheet (thickness 0.3 mm) which was to become a first substrate layer 22 was fabricated in a manner similar to that for fabrication of the third substrate layer 25.

Then, the green alumina sheet which was to become the second substrate layer 23 was sandwiched between the green alumina sheet which was to become the first substrate layer 22 and the green alumina sheet which was to become the third substrate layer 25 in the following manner: the conductor pattern which was to become the heating resistor 21 was sandwiched between the green alumina sheet which was to become the first substrate layer 22 and the green alumina sheet which was to become the second substrate layer 23; and the conductor pattern which was to become the conductor for retaining ionized elements 24 was sandwiched between the green alumina sheet which was to become the second substrate layer 23 and the green alumina sheet which was to become the third substrate layer 25. The resultant assembly was compression-bonded under reduced pressure, thereby yielding a substrate-forming green sheet from which ceramic heater bodies B were to be formed. In this state, the conductor patterns which were to become the connection electrodes 211 of the heating resistor 21 were electrically connected with the conductor patterns which were to become ceramic-heater-electricity-application terminals 232 via the through holes 231 and 233, etc.

(2) Firing and Formation of Porous Protective Layer

The thus-obtained substrate-forming green sheet was cut into five green laminates, which were to become ceramic heater bodies B. Subsequently, a paste including an alumina powder (70 g), an organic binder (polyvinyl butyral; 12 g), an organic solvent (butyl carbitol; 15 g), and a porosity-enhancing agent (a carbon powder (particle size 20 μm); 45 g) was applied, through printing (thickness 10 μm), to distal-end portions of the green laminates in such a manner as to cover at least four longitudinally extending edge portions 3 of the green laminates, followed by drying. Next, the green laminates were heated in the atmosphere while heating temperature was raised at a rate of 20° C. per hour, maintained at a maximum temperature of 450° C. for 1 hour so as to be debindered (so as to undergo a debinder process), and then fired at 1500° C. for 1 hour, thereby yielding precursors of a prismatic ceramic heater for heating a gas sensor element, each precursor having a bottom layer 41 of the porous protective layer 40 formed thereon. Next, a paste including an alumina powder (70 g), an organic binder (polyvinyl butyral; 12 g), an organic solvent (butyl carbitol; 25 g), and a porosity-enhancing agent (a carbon powder (particle size 5 μm); 30 g) was applied, through printing, dipping (viscosity is adjusted by use of butyl carbitol), or application, to the precursors of a prismatic ceramic heater in such a manner as to cover at least four longitudinally extending edge portions 3 of the precursors and such that the porous protective layer 40 obtained through firing assumes an above-mentioned predetermined thickness (including the thickness of the bottom layer 41) of 20 μm, 50 μm, 100 μm, and 200 μm, followed by drying. Next, the precursors were heated in the atmosphere while heating temperature was raised at a rate of 100° C. per hour, maintained at a maximum temperature of 900° C. for 1 hour, thereby yielding prismatic ceramic heaters 400 each having the porous protective layer 4 formed thereon.

4. Evaluation of Performance of Multilayered Gas Sensor Element and Prismatic Ceramic Heater

[1] Preliminary Test (1) An M 12 sensor-mounting threaded-hole was formed in an exhaust pipe provided under a 2000 cc engine in such a manner as to be directed perpendicularly to the axis of the exhaust pipe and such that a sensor was directed downward. (2) Carbon was applied to the surface of a sensor element of the present invention so as to facilitate checking for trace of water droplet; an ordinary protector (having holes of a 2 mm diameter) was attached to the sensor, thereby preparing a sensor sample; and the sensor sample was mounted into the mounting threaded-hole. (3) The engine was started and maintained at 1000 rpm for 10 minutes. (4) The engine was stopped, and the sensor element was removed and measured for the approximate diameter of a water droplet trace adhering to the sensor element. Notably, 20 sensor samples were prepared. (5) Water was dropped onto the sensor element by use of a dispenser so as to obtain the amount of a water droplet that might leave the water droplet trace observed in (4). As a result, the amount of adhering water was found to be not greater than 0.3 μl (microliters). Therefore, in a water drop test, which will be described later, the amount of water to be dropped on a sensor element was determined to be 0.3 μl and, as a severe condition, 1 μl.

The temperature of a sensor element and that of a ceramic heater as measured when water is to be dropped on the sensor element were determined to be 320° C., for the following reasons. (1) The temperature of exhaust gas must be low to the greatest possible extent while allowing presence of water. (2) The temperature of a sensor element or that of a ceramic heater must be not lower than a temperature at which the sensor element or the ceramic heater cracks upon adhesion of water.

[2] Water Drop Test

First, (1) a thermocouple having a diameter of 0.1 mm was attached by use of cement to the surface of a sensor element of the present embodiment (the surface located closer to the heating resistor 21; i.e., the surface opposite the surface where the electrode protection layer 5 is formed) or to the surface of a prismatic ceramic heater (the surface located closer to the heating resistor 332). Subsequently, (2) power was applied to the heating resistor 21 disposed within the sensor element or to the heating resistor 332 (the conductor for retaining ionized elements being of negative voltage) such that the thermocouple indicated 320° C. Next, (3) by use of a dispenser, water was dropped in an amount of 0.3 μl on a portion of the sensor element or prismatic ceramic heater in the vicinity of the attached thermocouple, the portion corresponding to the edge portion 3 of the element body A or prismatic ceramic heater B. Notably, samples whose resistance of the heating resistor is equivalent (±5%) to that of the sample to which the thermocouple was attached were selected. The same voltage as that at which the sample equipped with the thermocouple indicated a predetermined temperature was applied to these samples for the water drop test. Subsequently, (4) power to the heating resistor 21 or 332 was turned off, and, by use of color inspection liquid (aqueous red ink), the element body A or the prismatic ceramic heater B was visually observed for cracking of a portion where water was dropped. Steps (2) to (4) was repeated until cracking occurred. However, when no cracking occurred after repeating a series of steps (2) to (4) 10 times, no further repetition was carried out. Next, (5) the test was conducted similarly at an amount of water droplet of 1 μl. These tests were conducted on the multilayered gas sensor elements 100 or prismatic ceramic heaters 300 having a thickness of the porous protective layer 4 of 20 μm, 50 μm, 100 μm, and 200 μm as measured from the longitudinally extending edge portion 3 of the element body A or prismatic ceramic heater B. Ten multilayered gas sensor elements 100 or ten prismatic ceramic heaters 300 were tested for each of the thicknesses. These tests were also conducted on 10 multilayered gas sensor elements or 10 prismatic ceramic heaters, serving as Comparative Example, in which the porous protective layer 4 was not formed on the element body A or prismatic ceramic heater B. These tests were also conducted on the back surfaces of the gas sensor elements or prismatic ceramic heaters. The test results are shown in Tables 1 and 2. In Table 1, "number of cracked elements" means the number of sample elements suffering cracking among 10 tested sample elements of each type, and "number of repetitions till cracking" means the number of repetitions of the test sequence before the tested element was found to be cracked in observation of step (4). In Table 1, the porous protective layer 4 having a thickness of 20 μm, 50 μm, or 100 μm was formed in such a manner as to cover the entire surface of the element except the surface on which the electrode protection layer 5 was to be formed (i.e., the porous protective layer 4 was also formed on the entire back surface), whereas the porous protective layer having a thickness of 200 μm was formed in such a manner as to cover only four edge portions. In Table 2, the porous protective layer 4 having a thickness of 20 μm, 30 μm, 50 μm, or 100 μm was formed in such a manner as to cover the entire surface of the heater (i.e., the porous protective layer 4 was also formed on the entire back surface); and the porous protective layer having a thickness of 200 μm was formed such that a thickness of 100 μm was added to the existing porous protective layer of a 100 μm thickness only at the four edge portions. Further, the porous protective layer having a thickness of 20 μm was formed through thermal spraying of spinel in such a manner as to cover the entire surface of the heater (i.e., the porous protective layer 4 was also formed on the entire back surface).

TABLE 1

| | 0.3 μl | | | | 1 μl | | | |
| --- | --- | --- | --- | --- | --- | --- | --- | --- |
| | Edge portion | | Back surface | | Edge portion | | Back surface | |
| | Number of cracked elements | Number of repetitions till cracking | Number of cracked elements | Number of repetitions till cracking | Number of cracked elements | Number of repetitions till cracking | Number of cracked elements | Number of repetitions till cracking |
| No protective layer | 3/10 0/10 | 5, 8, 9 | 0/10 | — | 6/10 | 2, 4, 6, 7, 9, | 0/10 | — |
| 20 μm | 0/10 | | 0/10 | — | 1/10 | 10 | 0/10 | — |
| 50 μm | 0/10 | | 0/10 | — | 0/10 | — | 0/10 | — |
| 100 μm | 0/10 | | 0/10 | — | 0/10 | — | 0/10 | — |
| 200 μm | 0/10 | | 0/10 | — | 0/10 | — | 1/10 | 10 |

TABLE 2

| | 0.3 µl | | | | 1 µl | | | |
|---|---|---|---|---|---|---|---|---|
| | Edge portion | | Back surface | | Edge portion | | Back surface | |
| | Number of cracked elements | Number of repetitions till cracking | Number of cracked elements | Number of repetitions till cracking | Number of cracked elements | Number of repetitions till cracking | Number of cracked elements | Number of repetitions till cracking |
| No protective layer | 3/10 | 4, 8, 10 | 0/10 | — | 6/10 | 3, 4, 5, 8, 8, 9 | 1/10 | 10 |
| 20 µm | 0/10 | | 0/10 | — | 1/10 | 10 | 0/10 | — |
| 30 µm | 0/10 | | 0/10 | — | 0/10 | — | 0/10 | — |
| 50 µm | 0/10 | | 0/10 | — | 0/10 | — | 0/10 | — |
| 100 µm | 0/10 | | 0/10 | — | 0/10 | — | 0/10 | — |
| 200 µm | 0/10 | | 0/10 | — | 0/10 | — | 0/10 | — |
| 20 µm (thermal spraying) | 1/10 | 9 | 0/10 | — | 3/10 | 7, 10, 10 | 0/10 | — |

5. Effects of the Embodiment

As is apparent from the test results shown in Tables 1 and 2, almost all samples are free from cracking in the water drop test (0.3 µl and 1.0 µl) conducted on their back surfaces. However, in the case of the samples in which the porous protective layer 4 is not formed on its edge portions 3, three elements out of 10 are cracked in the water drop test conducted on the edge portion 3 at an amount of water droplet of 0.3 µl. Further, in the water drop test conducted at a severe amount of water droplet of 1 µl, more than half the samples are cracked. These test results indicate that a sample having no porous protective layer 4 formed thereon is prone to crack upon adhesion of water to at least the edge portion 3.

By contrast, the samples in which the porous protective layer having a thickness not less than 20 µm is formed on at least the edge portions 3 are free from cracking in the water drop test in which water was dropped on at least the edge portion 3 in an amount of 0.3 µl. These test results indicate that formation of the porous protective layer having a thickness not less than 20 µm on at least the edge portion 3 can prevent occurrence of cracking.

In the case of an amount of water droplet of 1 µl (severe water drop test), cracking occurred in the element in which the porous protective layer 4 had a thickness of 20 µm as measured at the edge portion 3, whereas the samples of Table 1 in which the porous protective layer 4 had a thickness of 50 µm as measured at the edge portion 3, and the samples of Table 2 in which the porous protective layer 4 had a thickness not less than 30 µm as measured at the edge portion 3, were free from cracking in the water drop test conducted on at least the edge portions. These test results indicate that imparting of a thickness not less than 50 µm to the porous protective layer 4 as measured at least the edge portion prevents cracking.

Even when the porous protective layer 4 is only formed on the edge portions 3 (in the case of the elements having a protective-layer thickness of 200 µm in Table 1), only one element cracked in the severe water droplet test conducted on its back surface as in the case of "No protective layer" in Table 2. These test results indicate that, even when the porous protective layer 4 is only formed on the edge portions, occurrence of cracking can be prevented. The porous protective layer of spinel formed through thermal spraying failed to exhibit expected protective effect even though its thickness was 20 µm.

Figure 10:
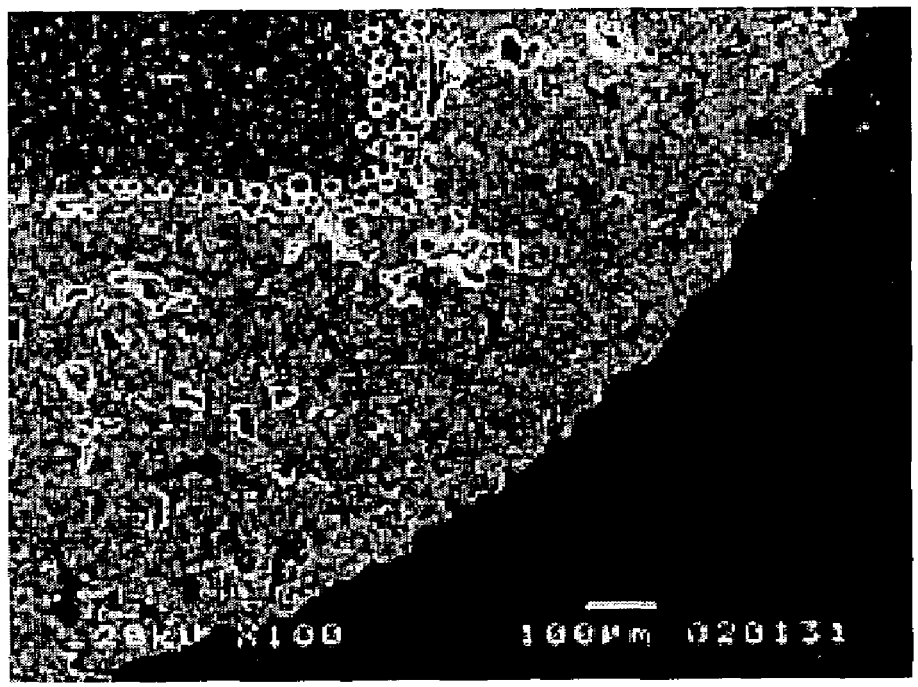
FIG. 10 is an enlarged sectional photo showing a porous protective layer formed on an edge portion of a prismatic gas sensor element of the present invention.

FIG. 10 is an enlarged photo showing an edge portion of a ceramic heater of a prismatic gas sensor of the present invention. The ceramic heater exhibits excellent water-induced-shock resistance and exfoliation resistance. As is apparent from FIG. 10, the porosity (and average pore diameter) of the porous protective layer differs such that the porosity (and average pore diameter) of the joining layer is greater than that of the layer overlying the joining layer. Further, a portion of the porous protective layer which covers an edge portion of substantially 90 degrees assumes an arcuate surface line having a radius of curvature not less than 10 µm.

The present invention is not limited to the above-described embodiments, but can be modified according to purposes and applications without departing from the spirit or scope of the invention. For example, the present invention is applicable to gas sensors other than oxygen sensors, such as CO sensors, $CO_2$ sensors, $NO_x$ sensors, humidity sensors, and ceramic heaters for use in these sensors as well as to sensors for automobile use and components of the sensors which must exhibit excellent resistance to thermal shock induced by contact with water. The present invention is also applicable to a gas sensor having three or more electrochemical cells such as an $NO_x$ sensor (which includes two oxygen-pumping cells and one oxygen sensor cell).

This application is based on Japanese Patent Application No. 2002-54554 filed Feb. 28, 2002, incorporated herein by reference in its entirety.

What is claimed is:

1. A laminated prismatic gas sensor element having a substantially rectangular cross section and comprising a ceramic heater which includes a heating resistor embedded in ceramic, and at least one solid electrolyte ceramic layer partially constituting a sensor cell having two electrodes, said gas sensor element being characterized in that at least part of a longitudinally extending edge portion having an angle of about 90 degrees of said gas sensor element, said part being located in the vicinity of said heating resistor, is coated with a porous protective layer having a porosity of 15%-65% and a thickness not less than 20 µm and is adapted to prevent cracking induced by contact with water.

2. The laminated prismatic gas sensor element as claimed in claim 1, wherein said electrolyte ceramic layer is made of an oxygen-ion-conductive zirconia ceramic.

3. The laminated prismatic gas sensor element as claimed in claim 1, wherein said porous protective layer is made of a porous ceramic having a porosity of 30%-60% and has a thickness of 20-500 μm.

4. The laminated prismatic gas sensor element as claimed in claim 1, wherein said porous protective layer is formed by firmly fixing a ceramic powder by firing to a surface, including an edge in the vicinity of said heating resistor, of said longitudinally extending edge portion of said gas sensor element, and the porous protective layer has a curved surface of a curvature radius not less than 10 μm.

5. The laminated prismatic gas sensor element as claimed in claim 1, wherein said porous protective layer comprises two or more porous layers.

6. The laminated prismatic gas sensor element as claimed in claim 5, wherein said porous protective layer comprises two or more porous layers of different porosities.

7. The laminated prismatic gas sensor element as claimed in claim 6, wherein said porous protective layer comprises a bottom layer directly formed on said gas sensor element and a surface layer exposed to an ambient atmosphere, and the porosity of said surface layer is lower than that of said bottom layer.

8. The laminated prismatic gas sensor element as claimed in claim 7, wherein the porosity of said bottom layer of said porous protective layer is at least twice as great as that of a layer located on or above said bottom layer.

9. The laminated prismatic gas sensor element as claimed in claim 5, wherein an average pore diameter of said bottom layer of said porous protective layer is at least twice as great as that of a layer located on or above said bottom layer.

10. The laminated prismatic gas sensor element as claimed in claim 1, wherein at least a portion of said porous protective layer is firmly fixed to an edge portion of said gas sensor element through simultaneous firing and another portion of said porous protective layer is fired at a temperature lower than that of said simultaneous firing.

11. The laminated prismatic gas sensor element as claimed in claim 1, wherein said ceramic heater is configured such that a heating resistor formed from a mixture of a noble metal and a ceramic is embedded in a ceramic laminate formed predominantly from alumina.

12. The laminated prismatic gas sensor element as claimed in claim 1, wherein an ion-migration-preventing electrode for preventing deterioration of said heating resistor is embedded in said ceramic, an electric potential of said ion-migration-preventing electrode is equal to or lower than that of said heating resistor, and said ion-migration-preventing electrode is disposed between said heating resistor and said porous protective layer.

13. The laminated prismatic gas sensor element as claimed in claim 1, wherein said porous protective layer is formed on an end portion of said prismatic gas sensor element so as to be exposed to exhaust gas, in the vicinity of said heating resistor, and said porous protective layer is not formed on at least the other end portion of said prismatic gas sensor element.

14. A gas sensor comprising a laminated prismatic gas sensor element as claimed in claim 13 and a sensor housing accommodating said prismatic gas sensor element, wherein said prismatic gas sensor element is fixedly supported by said sensor housing at a position where said porous protective layer is not formed.

* * * * *